US009914689B2

(12) United States Patent
Porcelli et al.

(10) Patent No.: US 9,914,689 B2
(45) Date of Patent: Mar. 13, 2018

(54) PROCESS FOR PRODUCTION OF ACRYLATES FROM EPOXIDES

(71) Applicant: Novomer, Inc., Boston, MA (US)

(72) Inventors: Richard V. Porcelli, Ithaca, NY (US); Jay J. Farmer, Ithaca, NY (US); Robert E. Lapointe, Ithaca, NY (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/291,011

(22) Filed: Oct. 11, 2016

(65) Prior Publication Data

US 2017/0247309 A1 Aug. 31, 2017

Related U.S. Application Data

(63) Continuation of application No. 14/753,457, filed on Jun. 29, 2015, now abandoned, which is a continuation of application No. 14/353,532, filed as application No. PCT/US2012/061791 on Oct. 25, 2012, now Pat. No. 9,096,510.

(60) Provisional application No. 61/551,496, filed on Oct. 26, 2011.

(51) Int. Cl.

| C08G 63/02  | (2006.01) |
| C07C 51/09  | (2006.01) |
| C07C 51/12  | (2006.01) |
| C07C 67/36  | (2006.01) |
| C08G 63/06  | (2006.01) |
| C08G 63/08  | (2006.01) |
| C07C 67/475 | (2006.01) |
| C07D 301/08 | (2006.01) |
| C07D 305/12 | (2006.01) |
| C08G 63/81  | (2006.01) |
| C08G 63/82  | (2006.01) |
| C07C 67/03  | (2006.01) |

(52) U.S. Cl.
CPC .............. *C07C 51/09* (2013.01); *C07C 51/12* (2013.01); *C07C 67/03* (2013.01); *C07C 67/36* (2013.01); *C07C 67/475* (2013.01); *C07D 301/08* (2013.01); *C07D 305/12* (2013.01); *C08G 63/06* (2013.01); *C08G 63/08* (2013.01); *C08G 63/81* (2013.01); *C08G 63/82* (2013.01); *C08G 63/823* (2013.01); *Y02P 20/125* (2015.11)

(58) Field of Classification Search
CPC .................................................... C07C 51/09
USPC ....................................................... 528/359
See application file for complete search history.

(56) References Cited

U.S. PATENT DOCUMENTS

| 2,352,641 A | 7/1944 | Kung |
| 2,361,036 A | 10/1944 | Kung |
| 2,376,704 A | 5/1945 | Kung |
| 2,422,728 A | 6/1947 | Gresham et al. |
| 2,449,995 A | 9/1948 | Gresham et al. |
| 2,466,501 A | 4/1949 | Steadman et al. |
| 2,469,704 A | 5/1949 | Stone |
| 2,485,510 A | 10/1949 | Redmon |
| 2,510,423 A | 6/1950 | Shaver |
| 2,548,155 A | 4/1951 | Gresham et al. |
| 2,623,067 A | 12/1952 | Beears et al. |
| 3,169,945 A | 2/1965 | Fritz et al. |
| 3,176,042 A | 3/1965 | Schnizer et al. |
| 3,326,938 A | 6/1967 | Wagner |
| 3,678,069 A | 7/1972 | Busker |
| 3,751,435 A | 8/1973 | Van der Ven et al. |
| 4,590,293 A | 5/1986 | Pascoe |
| 4,873,378 A | 10/1989 | Murphy et al. |
| 5,648,452 A | 7/1997 | Schechtman et al. |
| 6,133,402 A | 10/2000 | Coates et al. |
| 6,316,590 B1 | 11/2001 | Coates et al. |
| 6,392,078 B1 | 5/2002 | Ryu et al. |
| 6,538,101 B2 | 3/2003 | Coates |
| 6,608,170 B1 | 8/2003 | Coates |
| 6,852,865 B2 | 2/2005 | Coates et al. |
| 6,916,951 B2 | 7/2005 | Tustin et al. |

(Continued)

FOREIGN PATENT DOCUMENTS

| CN | 1132275 A | 10/1996 |
| CN | 1041591 C | 1/1999 |

(Continued)

OTHER PUBLICATIONS

International Preliminary Report on Patentability received for PCT Patent Application No. PCT/US2012/061791, dated May 8, 2014, 8 pages.

(Continued)

*Primary Examiner* — Terressa Boykin

(74) *Attorney, Agent, or Firm* — Morrison & Foerster LLP

(57) ABSTRACT

In one aspect, the present invention encompasses integrated processes for the conversion of epoxides to acrylic acid derivatives and polyesters. In certain embodiments, the methods of the present invention comprise the steps of: providing a feedstock stream comprising an epoxide and carbon monoxide; contacting the feedstock stream with a metal carbonyl in a first reaction zone to effect conversion of at least a portion of the provided epoxide to a beta lactone; directing the effluent from the first reaction zone to a second reaction zone where the beta lactone is subjected to conditions that convert it to a compound selected from the group consisting of: an alpha beta unsaturated acid, an alpha beta unsaturated ester, an alpha beta unsaturated amide, and an optionally substituted polypropiolactone polymer; and isolating a final product comprising the alpha-beta unsaturated carboxylic acid, the alpha-beta unsaturated ester, the alpha-beta unsaturated amide or the polypropiolactone.

57 Claims, 2 Drawing Sheets

(56) References Cited

U.S. PATENT DOCUMENTS

| | | |
|---|---|---|
| 8,445,703 B2 | 5/2013 | Allen et al. |
| 8,796,475 B2 | 8/2014 | Allen et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 2003/0098274 A1 | 5/2003 | Lee et al. |
| 2003/0162961 A1 | 8/2003 | Coates et al. |
| 2005/0014977 A1 | 1/2005 | Drent et al. |
| 2005/0240031 A1 | 10/2005 | Cavani et al. |
| 2005/0240032 A1 | 10/2005 | Luinstra et al. |
| 2005/0256320 A1 | 11/2005 | Luinstra et al. |
| 2007/0217965 A1 | 9/2007 | Johnson et al. |
| 2007/0293695 A1 | 12/2007 | Zoeller et al. |
| 2009/0124787 A1 | 5/2009 | Preishuber-Pfluql et al. |
| 2009/0253934 A1 | 10/2009 | Ho et al. |
| 2011/0319849 A1 | 12/2011 | Collias et al. |
| 2012/0123137 A1 | 5/2012 | Allen et al. |
| 2013/0165670 A1 | 6/2013 | Allen et al. |
| 2013/0281715 A1 | 10/2013 | Allen et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen et al. |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |

FOREIGN PATENT DOCUMENTS

| | | |
|---|---|---|
| EP | 0352850 | 1/1990 |
| EP | 0441447 A1 | 8/1991 |
| EP | 0577206 A2 | 1/1994 |
| EP | 0688806 A2 | 12/1995 |
| EP | 2325214 A1 | 5/2011 |
| GB | 994091 A | 6/1965 |
| JP | 2-104579 A | 4/1990 |
| JP | 2006-500339 A | 1/2006 |
| JP | 2013-173090 A | 9/2013 |
| WO | 2004/012860 A1 | 2/2004 |
| WO | 2010/118128 A1 | 10/2010 |
| WO | 2012/030619 A1 | 3/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |

OTHER PUBLICATIONS

Kaesz et al., "Hydride complexes of the transition metals", Chemical Review, vol. 72, No. 3, 1972, pp. 231-281.

Agostini et al., Synthesis and Characterization of Poly-β-Hydroxybutyrate. I. Synthesis of Crystalline DL-Poly-β-Hydroxybutyrate from DL-β-Butyrolactone, Journal of Polymer Science, Part A-1, vol. 9, No. 10,1971, pp. 2775-2787.

Billingham et al., Polymerization and Copolymerizationof β-Butyrolactone by Aluminium Compounds, Journal of Organometallic Chemistry, vol. 341, No. 1-3,1988, pp. 83-89.

Extended European Search Report (includes Supplementary European Search Report and Search Opinion) received for European Patent Application No. 12842768.9 dated May 28, 2015, 6 pages.

Gross et al., Polymerization of .Beta.-Monosubstituted-.Beta.-Propiolactones using Trialkylaluminum-Water Catalytic Systems and Polymer Characterization, Macromolecules, vol. 21, No. 9, 1988, pp. 2657-2668.

Hori et al., Ring-Opening Polymerization of Optically Active .Beta.- Butyrolactone using Distannoxane Catalysts: Synthesis of High-Molecular-Weight Poly(3-Hydroxybutyrate), Macromolecules, vol. 26, No. 20, 1993, pp. 5533-5534.

International Search Report and Written Opinion received for PCT Patent Application No. PCT/US13/25683, dated Apr. 23, 2013, 8 pages.

International Search Report and Written Opinion received for PCT Patent Application No. PCT/US2010/030230, dated Jun. 10, 2010, 17 pages.

International Search Report and Written Opinion received for PCT Patent Application No. PCT/US2011/049125, dated Jan. 11, 2012, 10 pages.

International Search Report and Written Opinion received for PCT Patent Application No. PCT/US2012/061791, dated Feb. 8, 2013, 10 pages.

International Search Report and Written Opinion received for PCT Patent Application No. PCT/US2013/026810, dated Apr. 30, 2013, 8 pages.

International Search Report and Written Opinion received for PCT Patent Application No. PCT/US2013/049026, dated Dec. 17, 2013, 9 pages.

Kowalczuk et al., New reactions of potassium naphthalenide with .beta.-, .gamma.- and .delta.-lactones: an efficient route to .alpha.-alkyl .gamma.- and .delta.-lactones and .alpha.,.beta.-unsaturated carboxylic acid esters, Journal of Organic Chemistry, vol. 57, No. 1, 1992, pp. 389-391.

Non-Final Office Action received for U.S. Appl. No. 14/353,532, dated Nov. 7, 2014, 9 pages.

Non-Final Office Action received for U.S. Appl. No. 14/753,457, dated Apr. 11, 2016, 8 pages.

Notice of Allowance received for U.S. Appl. No. 14/353,532, dated May 21, 2015, 5 pages.

Rieth et al., Single-Site Beta-Diiminate Zinc Catalysts for the Ring-Opening Polymerization of Beta-Butyrolactone and Beta-Valerolactone to Poly(3-Hydroxyalkanoates), Journal of the American Chemical Society, vol. 124, No. 51,2002, pp. 15239-15248.

Rowley et al., Catalytic Double Carbonylation of Epoxides to Succinic Anhydrides: Catalyst Discovery, Reaction Scope, and Mechanism, Journal of the American Chemical Society, vol. 129, 2007, pp. 4948-4960.

Schechtman et al., Chemical Synthesis of Isotactic Poly(3-Hydroxyalkanoates), Division of Polymer Chemistry, vol. 40, No. 1,1999, pp. 508-509.

Slowik et al., Catalytic Conversion of Waste Carbon Monoxide to Valuable Chemicals & Materials, Technical Proceedings of the Clean Technology Conference and Trade Show, 2010, pp. 283-286.

Tanahashi et al., Thermal Properties and Stereoregularity of Poly(3-Hydroxybutyrate) prepared from Optically Active .Beta.-Butyrolactone with a Zinc-based Catalyst, Macromolecules, vol. 24, No. 20, 1991, pp. 5732-5733.

Zhang et al., Stereochemistry of the Ring-Opening Polymerization of (S)- .Beta.-Butyrolactone, Macromolecules, vol. 23, No. 13, 1990, pp. 3206-3212.

PROCESS FOR PRODUCTION OF ACRYLATES FROM EPOXIDES

CROSS-REFERENCE TO RELATED APPLICATIONS

This application is a continuation of U.S. patent application Ser. No. 14/753,457, filed on Jun. 29, 2015, which is a continuation of U.S. patent application Ser. No. 14/353,532 (now U.S. Pat. No. 9,096,510, issued on Aug. 4, 2015), which is a U.S. National Stage application of PCT/US2012/061791, filed internationally on Oct. 25, 2012, which claims priority to U.S. Provisional Patent Application No. 61/551,496, filed on Oct. 26, 2011, each of which is hereby incorporated by reference in its entirety.

FIELD OF THE INVENTION

The invention pertains to the field of chemical synthesis. More particularly, the invention pertains to an integrated process for the production of acrylic acid and its derivatives by carbonylation of epoxide feedstocks.

BACKGROUND OF THE INVENTION

Beta lactones are a class of chemical compounds that have great industrial potential For example, beta lactones (e.g., beta propiolactone (BPL)) can undergo reactions to produce valued chemical derivatives, including 3-hydroxypropionic acid and its esters, propanediol, acrylic acid, acrylate esters and amides, succinic anhydride, succinic acid, butanediol, polypropiolactone biodegradable polymers, and others. It also has some industrial uses itself as a specialty disinfectant to sterilize medical products.

However, since beta propiolactone has been difficult to manufacture in a selective and high yielding fashion and because it has been found to be a probable human carcinogen, the use of this highly interesting and reactive chemical intermediate is limited. Some previous commercial applications which otherwise represented economically attractive processes, such as the manufacture of acrylic acid and its esters, have been phased out in favor of other alternatives. In the case of acrylic acid manufacture, the industry has turned to propylene oxidation. For many years propylene was a low cost feedstock and alternate routes to acrylic acid were of little interest. However because propylene production is tightly tied to petroleum refining its price fluctuates with crude oil prices. Propylene availability is further impacted by demands for other product in the refiningetroleum industry. As a result propylene prices have risen sharply in recent years. This dynamic has prompted interest in alternate routes to acrylic acid. The use of ethylene oxide (EO) as a feedstock for acrylic acid is increasingly attractive since EO can be derived from inexpensive ethylene sourced from natural gas production. Carbonylation of EO can provide beta propiolactone in excellent yield and selectivity, however the problems of handling and transporting this toxic chemical still remain.

In order to take advantage of the unique chemical properties of beta propiolactone, which is just one example of the class of similar lactones which includes beta butyrolactone and other interesting lactone chemical intermediates, it is desired to develop integrated processes in which the purification or isolation of beta propiolactone is avoided.

It is therefore a broad object of this invention to provide the integrated production and conversion of beta lactones, without their intermediate separation, with the aim of avoiding the potential exposure to the hazards of some of the class of lactones, while at the same time providing economically advantageous production processes.

Commercially, beta propiolactone has in the past been produced by the reaction of ketene with formaldehyde. The production of ketene is based on the high temperature (700-750° C.) thermal dissociation of acetic acid in the presence of triethyl phosphate under a reduced pressure. This ketene process is mechanically complex, highly energy intensive and is a source of unwanted emissions to the atmosphere. After isolation, highly reactive monomeric ketene can be reacted with aldehydes to form beta lactones in the presence of aluminum chloride catalyst, commonly referred to as a Friedal-Crafts catalyst.

Reaction of ketene and formaldehyde yields beta propiolactone. Reaction with acetaldehyde produces beta butyrolactone, while reaction with crotonaldehyde forms a polyester which is then thermally decomposed to sorbic acid. The aluminum chloride itself has many hazards it use, including potentially violent reactions of anhydrous aluminum chloride with water or bases. This very active catalyst also results in the formation of a number of unwanted byproducts that must be separated and removed from the desired lactone product leading to further handling challenges and additional opportunities for worker exposure. A general problem with the use of aluminum chloride Friedal-Crafts catalyst is that it is often consumed in the reaction, is very difficult to recover and regenerate, and commonly must be destroyed after use, generating a large amount of corrosive waste.

Therefore, it is advantageous to rely on a better process for the production of beta lactones, and more particularly the intermediate, beta propiolactone, by the carbonylation of the corresponding epoxide, particularly ethylene oxide in the case of beta propiolactone.

SUMMARY OF THE INVENTION

In certain embodiments, the present invention provides methods for the production of derivatives of beta lactones (e.g., beta propiolactone) by integrating their production, for example by the carbonylation of ethylene oxide, with the conversion of beta propiolactone to acrylic acid, as one example of a number of possible valued derivatives. In certain embodiments, the invention provides integrated processes for the conversion of ethylene oxide and carbon monoxide to acrylic acid and its esters without the need to isolate beta propiolactone as a separate intermediate product.

Applied to epoxides, such as ethylene oxide, carbonylation results in the simultaneous opening of the epoxide ring and the addition of carbon in the form of a carbonyl (C=O) functional group, resulting in the formation of a beta propiolactone by the general reaction

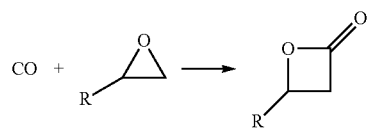

Examples include:

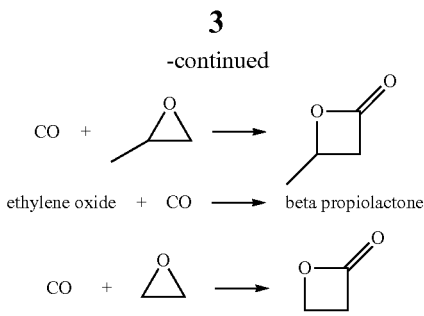

The carbonylation of epoxides can be catalyzed by metal carbonyls, most commonly Group VIII carbonyls and, in particular carbonyls of cobalt, at modest temperature and pressure. The carbonylation reaction can be run in the liquid phase with either a homogeneous (i.e., soluble) catalyst complex, or with a heterogeneous (i.e., active cobalt carbonyl fixed on a solid support) catalyst. The reaction can also be run in the vapor phase, using a heterogeneous, supported form of the cobalt catalyst.

If the goal is the production of acrylic acid or acrylate esters, beta propiolactone undergoes thermolysis or alcoholysis respectively. One example is to react beta propiolactone with phosphoric acid using a copper powder catalyst at 140-180° C. and 25-250 bar to quantitatively form acrylic acid—this reaction is sometimes catalyzed by water. If the same reaction is run in the presence of an alcohol, the corresponding acrylate ester is formed directly. The thermolysis of beta propiolactone was in fact used as the basis for Celanese Corporation's production of about 35,000 tons/year of purified acrylic acid and its esters between 1957 and 1974. In that example, beta propiolactone was first isolated from the product of the reaction of formaldehyde with ketene, with the potential of worker exposure and environmental release of the hazardous intermediate, as the requirement of a high purity of final acrylic acid or acrylate ester product mandated the purification of the intermediate beta propiolactone to a high specification.

This invention makes it possible to eliminate the hazards and costs associated with isolating the intermediate lactone by choosing the appropriate carbonylation and thermolysis process and conditions to allow a direct linking of the two reaction steps.

In certain embodiments, the process of this invention can also be directly integrated to the formation of ethylene oxide, thus avoiding the isolation and storage of this toxic and potentially explosive intermediate. In certain embodiments, the processes of the present invention are fed by ethylene gas which is converted to ethylene oxide in a first reaction zone, the ethylene oxide from the first zone then feeds a second reaction zone where carbonylation takes place to yield BPL, the effluent from the second reaction zone is then fed to a third stage where the BPL is converted to acrylic acid or related acrylate derivatives.

In certain embodiments, the present invention provides a method for the synthesis of acrylic acid comprising the steps of:
  providing a gaseous feedstock stream comprising ethylene oxide and carbon monoxide;
  directing the feedstock stream to a first reaction zone where it is contacted with a metal carbonyl compound and where at least a portion of the ethylene oxide is converted to a carbonylation product stream comprising beta propiolactone;
  directing the carbonylation product stream to a second reaction zone where it is contacted with a catalyst which catalyzes the conversion of beta propiolactone to acrylic acid;
  withdrawing an acrylic acid product stream from the second reaction zone; and
  isolating acrylic acid from the product stream.

In other embodiments, the present invention provides a method for the synthesis of polypropiolactone comprising the steps of:
  providing a gaseous feedstock stream comprising ethylene oxide and carbon monoxide;
  directing the feedstock stream to a first reaction zone where it is contacted with a metal carbonyl compound and at least a portion of the ethylene oxide is converted to a product stream comprising beta propiolactone;
  directing the product stream comprising beta propiolactone to a polymerization reactor containing a suitable optional solvent and a polymerization catalyst;
  withdrawing a polypropiolactone product stream from the polymerization reactor; and
  isolating polypropiolactone from the product stream.

In another embodiment, the present invention provides a method for the synthesis of poly-3-hydroxybutyrate comprising the steps of:
  providing a gaseous feedstock stream comprising enantioenriched propylene oxide and carbon monoxide;
  directing the feedstock stream to a first reaction zone where it is contacted with a metal carbonyl compound and at least a portion of the propylene oxide is converted to a product stream comprising beta butyrolactone;
  directing the product stream comprising beta butyrolactone to a polymerization reactor containing an optional solvent and a polymerization catalyst;
  withdrawing a poly-3-hydroxybutyrate product stream from the polymerization reactor; and
  isolating poly-3-hydroxybutyrate from the product stream.

DEFINITIONS

Figure 1:
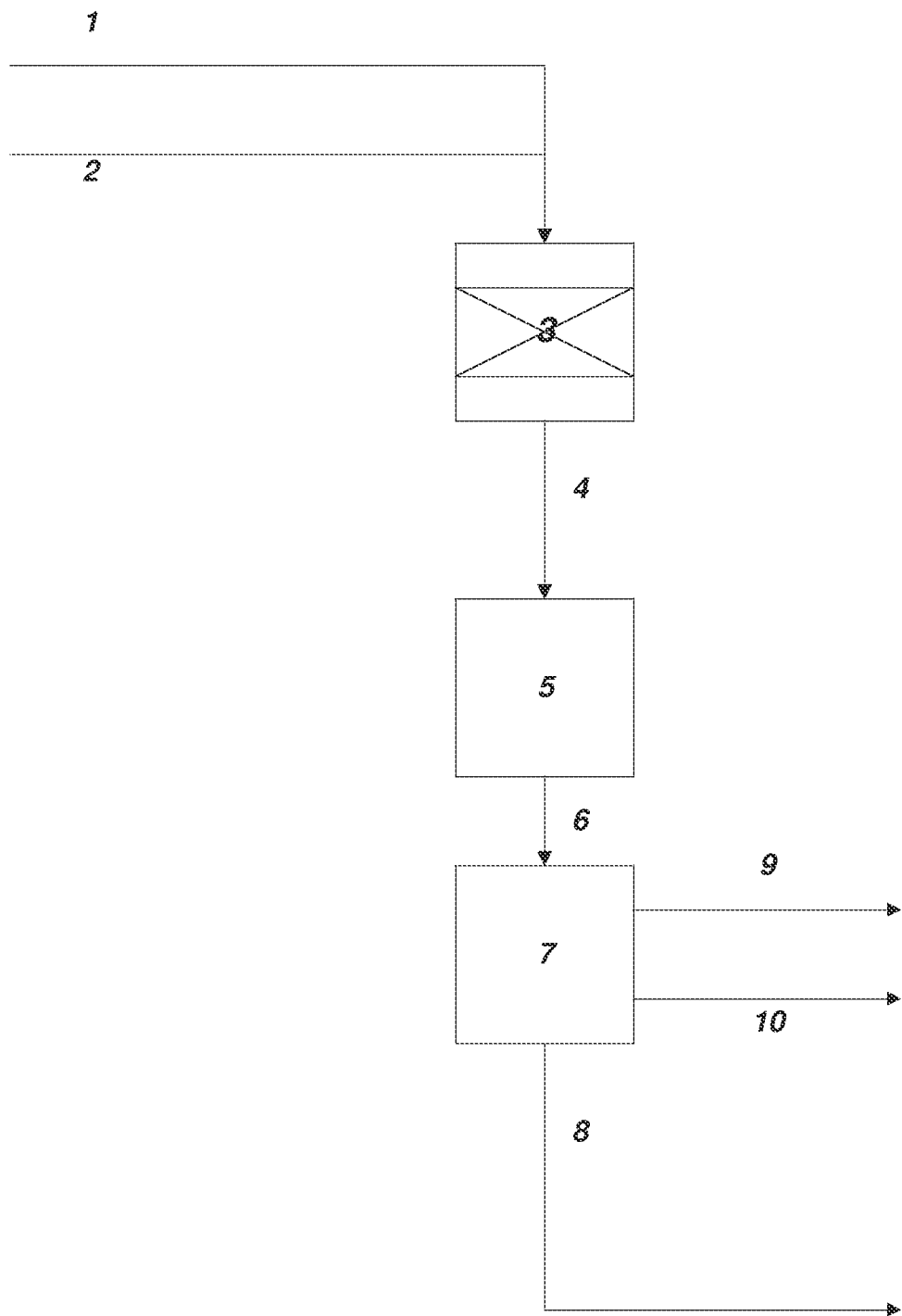
FIG. 1 shows a process schematic for production of beta lactone from an epoxide using a supported catalyst.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various stereoisomeric forms, e.g., enantiomers and/or diastereomers. Thus, inventive compounds and compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of enantiomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of enantiomers.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an stereoisomer may, in some embodiments, be provided substantially free of one or more corresponding stereoisomers, and may also be referred to as "stereochemically enriched."

Where a particular enantiomer is preferred, it may, in some embodiments be provided substantially free of the opposite enantiomer, and may also be referred to as "optically enriched." "Optically enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms. In some embodiments, aliphatic groups contain 1-4 carbon atoms. In some embodiments, aliphatic groups contain 1-3 carbon atoms. In some embodiments, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or bicyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, the term "3- to 8-membered carbocycle" refers to a 3- to 8-membered saturated or partially unsaturated monocyclic carbocyclic ring. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring. In certain embodiments, the term "$C_{3-20}$ carbocycle" refers to a 3- to 8-membered saturated or partially unsaturated monocyclic carbocyclic ring, or a 7- to 20-membered saturated or partially unsaturated polycyclic carbocyclic ring.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms. In some embodiments, alkyl groups contain 1-4 carbon atoms. In certain embodiments, alkyl groups contain 1-3 carbon atoms. In some embodiments, alkyl groups contain 1-2 carbon atoms. Examples of alkyl radicals include, but are not limited to, methyl, ethyl, n-propyl, iso-propyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms. In some embodiments, alkenyl groups contain 2-4 carbon atoms. In some embodiments, alkenyl groups contain 2-3 carbon atoms. In some embodiments, alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms. In some embodiments, alkynyl groups contain 2-4 carbon atoms. In some embodiments, alkynyl groups contain 2-3 carbon atoms. In some embodiments, alkynyl groups contain 2 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_{6-10}$ aryl" refer to a phenyl or an 8- to 10-membered polycyclic aryl ring. In certain embodiments, the term "6- to 12-membered aryl" refers to a phenyl or an 8- to 12-membered polycyclic aryl ring. In certain embodiments, the tem "$C_{6-14}$ aryl" refers to a phenyl or an 8- to 14-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the terms "5- to 10-membered heteroaryl" refers to a 5- to 6-membered heteroaryl ring having 1 to 3 heteroatoms independently selected from nitrogen, oxygen, or sulfur, or an 8- to 10-membered bicyclic heteroaryl ring having 1 to 4 heteroatoms independently selected from nitrogen, oxygen, or sulfur. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 8-membered heterocycle" refers to a 3- to 8-membered saturated or partially unsaturated monocyclic heterocyclic ring having 1 to 2 heteroatoms independently selected from nitrogen, oxygen, or sulfur. In some embodiments, the term "3- to 12-membered heterocyclic" refers to a 3- to 8-membered saturated or partially unsaturated monocyclic heterocyclic ring having 1 to 2 heteroatoms independently selected from nitrogen, oxygen, or sulfur, or a 7- to 12-membered saturated or partially unsaturated polycyclic heterocyclic ring having 1-3 heteroatoms independently selected from nitrogen, oxygen, or sulfur. In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond.

The term "partially unsaturated" is intended to encompass rings having multiple sites of unsaturation, but is not intended to include aryl or heteroaryl moieties, as herein defined.

One of ordinary skill in the art will appreciate that the synthetic methods, as described herein, may utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In some embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. By way of non-limiting example, hydroxyl protecting groups include methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzo furan-2-yl, 1-ethoxy ethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis (4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzo dithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzylcarbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are described by Greene and Wuts (infra).

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°C(O)NR°_2$; —$N(R°)N(R°)C(O)OR°$; —$(CH_2)_{04}C(O)R°$; —$C(S)R°$; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)$ NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3- to 12-membered saturated, partially unsaturated, or aryl mono or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, (haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-4}$C(O)N(R°)$_2$; —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, (CH$_2$)$_{0-2}$NR$^•_2$, —NO$_2$, —SiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur.

Suitable substituents on the aliphatic group of R* include halogen, R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3- to 12-membered saturated, partially unsaturated, or aryl mono or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms independently selected from nitrogen, oxygen, or sulfur.

By 'carbonylation', we refer to reactions that add carbon monoxide to an organic compound, thus increasing the organic substrate molecule by one carbon atom. Furthermore, the resulting compounds contain the C=O carbonyl functional group.

DETAILED DESCRIPTION OF CERTAIN EMBODIMENTS

In one aspect, the present invention encompasses integrated processes and methods for the conversion of epoxides to acrylic acid derivatives and polyesters. In another aspect, the invention provides systems suitable for effecting the conversion of epoxides to acrylic acid derivatives and polyesters.

I. Methods of the Invention

In certain embodiments, the present invention encompasses methods for the conversion of epoxides to acrylates and related products. In certain embodiments, the methods comprise the steps of:
  i) providing a feedstock stream comprising an epoxide and carbon monoxide;
  ii) contacting the feedstock stream with a metal carbonyl in a first reaction zone to effect conversion of at least a portion of the provided epoxide to a beta lactone;
  iii) directing the effluent from the first reaction zone to a second reaction zone where the beta lactone is subjected to conditions that convert it to a compound selected from the group consisting of: an alpha beta unsaturated acid, an alpha beta unsaturated ester, an alpha beta unsaturated amide, and an optionally substituted polypropiolactone polymer; and
  iv) isolating a final product comprising the alpha-beta unsaturated carboxylic acid, the alpha-beta unsaturated ester, the alpha-beta unsaturated amide or the polypropiolactone,
  where the composition of the feedstock stream, the identity of the metal carbonyl the composition of the effluent from the first reaction zone, the identity of the conditions in the second reaction zone and the manner of isolation are as defined hereinbelow and in the classes and subclasses herein.

The sections below describe more fully each step of the method and the conditions utilized to effect each step.

Ia) The Feedstock Stream

The first reaction stage (i.e. the stage fed by the epoxide feedstock stream) is also referred to herein as the carbonylation stage. The purpose of this stage is to convert the epoxide fed into the stage into a beta lactone by carbonylation.

As noted above, the feedstock stream contains an epoxide and carbon monoxide. In certain embodiments, the feedstock stream comprises a $C_{2-20}$ aliphatic or aromatic epoxide. In certain embodiments, the feedstock stream comprises a $C_{2-12}$ aliphatic epoxide. In certain embodiments, the feedstock stream comprises an epoxide selected from the group consisting of: ethylene oxide, propylene oxide, 1-butylene oxide, 2-butylene oxide, 1-hexene oxide, 1-octene oxide, epichlorohydrin, and mixtures of two or more of these. In certain embodiments, the feedstock stream comprises ethylene oxide. In certain embodiments, the feedstock stream comprises propylene oxide.

In certain embodiments, the feedstock stream comprises a gaseous mixture containing epoxide and carbon monoxide. In certain embodiments, the molar ratio of carbon monoxide to epoxide in feedstock stream ranges from about 1:1 to about 10,000:1. In certain embodiments, the molar ratio of carbon monoxide to epoxide in feedstock stream is about 5000:1, is about 2500:1, is about 2000:1, is about 1500:1, is about 1000:1, is about 500:1, is about 1:500, is about 200:1, is about 100:1, is about 50:1, is about 20:1, is about 10:1, is about 5:1 or is about 1:1. In some embodiments, the ratio of carbon monoxide to epoxide is selected, based on other reaction conditions, so that the reaction proceeds in an economical and time-feasible manner. In some embodiments, the ratio of carbon monoxide to epoxide in the feedstock stream is between about 1:1 to about 100:1. In some embodiments, the ratio of carbon monoxide to epoxide in the feedstock stream is between about 1:1 to about 1000:1. In some embodiments, the ratio of carbon monoxide to epoxide in the feedstock stream is between about 10:1 to about 1000:1. In some embodiments, the ratio of carbon monoxide to epoxide in the feedstock stream is between about 10:1 to about 10,000:1. In some embodiments, the ratio of carbon monoxide to epoxide in the feedstock stream is between about 100:1 to about 1000:1. In some embodiments, the ratio of carbon monoxide to epoxide in the feedstock stream is between about 10:1 to about 1000:1. In some embodiments, the ratio of carbon monoxide to epoxide in the feedstock stream is between about 10:1 to about 500:1. In some embodiments, the ratio of carbon monoxide to epoxide in the feedstock stream is between about 10:1 to about 100:1. In some embodiments, the ratio of carbon monoxide to epoxide in the feedstock stream is between about 10:1 to about 50:1. In some embodiments, the ratio of carbon monoxide to epoxide in the feedstock stream is between about 20:1 to about 200:1. In some embodiments, the ratio of carbon monoxide to epoxide in the feedstock stream is between about 50:1 to about 200:1.

In certain embodiments, the gaseous feedstock stream comprises ethylene oxide (EO) and carbon monoxide (CO). In certain embodiments, the gaseous EO/CO stream is provided at a temperature, pressure, and EO:CO gas ratio such that the mixture is above the dew point of ethylene oxide. In certain embodiments, the gaseous EO/CO mixture comprises a greater partial pressure of carbon monoxide than ethylene oxide. In certain embodiments, the EO/CO gaseous feedstock stream is heated to maintain a temperature and pressure at which the ethylene oxide remains in the gas phase. Determining compositions, temperatures and pressures at which the EO/CO feedstock stream remains gaseous is within the capability of the skilled artisan, these mixtures can be determined experimentally, or by reference to the phase diagram of ethylene oxide.

In certain embodiments, the feedstock stream further comprises one or more additional components. In certain embodiments, the additional components comprise diluents which do not directly participate in the chemical reactions of the epoxide or its derivatives. In certain embodiments, such diluents may include one or more inert gases (e.g. nitrogen, argon, helium and the like) or volatile organic molecules such as hydrocarbons, ethers, and the like. In certain embodiments, the feed stream may comprise hydrogen, traces of carbon dioxide, methane, and other compounds commonly found in industrial carbon monoxide streams. In certain embodiments, the feed stream may further comprise materials that may have a direct or indirect chemical function in one or more of the processes involved in the conversion of the epoxide to various end products. In certain embodiments, such functional materials may include, but are not limited to: volatile metal carbonyl compounds (e.g. $HCo(CO)_4$) and the like), protic compounds (e.g. water or alcohols), and stabilizers (e.g. amine bases, phosphorous compounds and the like).

Additional reactants can include mixtures of carbon monoxide and another gas. In some embodiments, carbon monoxide is provided in a mixture with hydrogen (e.g., Syngas). The ratio of carbon monoxide and hydrogen can be any ratio, including by not limited to 1:1, 1:2, 1:4, 1:10, 10:1, 4:1, or 2:1. The carbon monoxide sources include but are not limited to: wood gas, producer gas, coal gas, town gas, manufactured gas, hygas, Dowson gas or water gas, among others. In some embodiments, the carbon monoxide is provided at super-atmospheric pressure. The quantity of carbon monoxide should be supplied to effect efficient conversion of the epoxide starting material to a beta-lactone.

In certain embodiments, the feedstock stream is characterized in that it is essentially free of oxygen. In certain embodiments, the feedstock stream is characterized in that it is essentially free of water. In certain embodiments, the feedstock stream is characterized in that it is essentially free of oxygen and water.

In certain embodiments, the feedstock stream provided in step i) of the above-described process comprises ethylene oxide. In certain embodiments, the ethylene oxide in the feedstock stream is obtained directly from the gas phase oxidation of ethylene. This embodiment is advantageous in that it avoids the need to isolate, store, and transport ethylene oxide which is both toxic and explosive. In certain embodiments, the ethylene oxide is maintained in the gas phase as produced and fed to the carbonylation stage without condensing it to a liquid. Thus, in certain embodiments, the present invention encompasses methods for the conversion of ethylene gas to acrylic acid or its derivatives, the process comprising the steps of:

feeding ethylene to an oxidation stage to produce a reaction stream comprising ethylene oxide (preferably using known commercial processes such as oxidation by $O_2$ in the presence of silver);

contacting the ethylene oxide-containing stream with carbon monoxide in the presence of a metal carbonyl compound in a second stage to provide a product stream comprising beta propiolactone; and directing the beta propiolactone-containing product stream to a conversion stage where it is subjected to conditions to convert it to a final product selected from the group consisting of: acrylic acid, an acrylate ester, an acrylamide, and polypropiolactone.

In certain embodiments, the ethylene oxide feedstock stream is first treated to remove water. In certain embodiments, the ethylene oxide feedstock stream is first treated to remove carbon dioxide. In certain embodiments, the method includes a step of adding carbon monoxide to the ethylene oxide stream. In certain embodiments, this addition of carbon monoxide is done before the ethylene oxide stream enters the carbonylation stage.

Ib) Catalysts

As noted above, the first reaction stage comprises at least one metal carbonyl compound. Typically, a single metal carbonyl compound is provided, but in certain embodiments, mixtures of two or more metal carbonyl compounds are provided. Preferably, the provided metal carbonyl compound is capable of ring-opening an epoxide and facilitating the insertion of carbon monoxide into the resulting metal carbon bond. Metal carbonyl compounds with this reactivity are well known in the art and are used for laboratory experimentation as well as in industrial processes such as hydroformylation.

In some embodiments, a metal carbonyl compound in the carbonylation stage of the process comprises a compound with the general formula $[QM_y(CO)_w]^x$, where:

Q is any ligand or more than one ligand and need not be present;

M is a metal atom;

y is an integer from 1 to 6 inclusive;

w is a number such as to provide the stable metal carbonyl; and x is an integer from −3 to +3 inclusive.

In certain embodiments where a metal carbonyl compound has the formula $[QM_y(CO)_w]^x$, M is selected from the group consisting of Ti, Cr, Mn, Fe, Ru, Co, Rh, Ni, Pd, Cu, Zn, Al, Ga and In. In certain embodiments, M is Co.

In certain embodiments, metal carbonyl compound in the carbonylation stage comprises a Group 9 metal carbonyl. In certain embodiments, the Group 9 metal carbonyl compound is selected from the group consisting of $Co_2(CO)_8$, $Co_4(CO)_{12}$, $Rh_4(CO)_{16}$, $Ir_4(CO)_{12}$ and mixtures of two or more of these. In certain embodiments, the metal carbonyl comprises a cobalt compound. In certain embodiments, the Group 9 metal carbonyl compound comprises the moiety $Co(CO)_4^-$.

In certain embodiments, a provided metal carbonyl compound comprises an anionic metal carbonyl moiety (i.e. x is a negative integer). In other embodiments, a provided metal carbonyl compound comprises a neutral metal carbonyl compound (i.e. x is zero). In certain embodiments, a provided metal carbonyl compound comprises a metal carbonyl hydride. In some embodiments, a provided metal carbonyl compound acts as a pre-catalyst which reacts in situ with one or more reaction components, additives, or solid supports, to provide an active species different from the compound initially provided. Such pre-catalysts are specifically encompassed by the present invention as is the recognition that the active species in a given reaction may not be known with certainty, thus the identification of such a reactive species in situ, does not itself depart from the spirit or teachings of the present invention.

In certain embodiments where the metal carbonyl compound comprises an anionic metal carbonyl species, the metal carbonyl species has the general formula $[QM_y(CO)_{w^*}]^{z-}$, where Q, M, and y are as defined above and in the classes and subclasses described herein, w* is an integer such as to provide a stable anionic metal carbonyl, and z is an integer from 1 to 3.

In certain embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In certain embodiments, the anionic metal carbonyl comprises $[Co(CO)_4]^-$. In some embodiments, a mixture of two or more anionic metal carbonyl complexes may be present in the carbonylation stage.

The term "such as to provide a stable anionic metal carbonyl" for $[QM_y(CO)_{w^*}]^{z-}$, is used herein to mean that $[QM_y(CO)_{w^*}]^{z-}$ is a species characterizable by analytical means, e.g., NMR, IR, X-ray crystallography, Raman spectroscopy and/or electron spin resonance (EPR) or is isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for carbon monoxide to coordinate and therefore the value of w*. Typically, such compounds conform to the "18-electron rule". Such knowledge is within the grasp of one having ordinary skill in the arts pertaining to the synthesis and characterization of metal carbonyl compounds.

In embodiments where the provided metal carbonyl compound is an anionic species, one or more cations must also necessarily be present. The present invention places no particular constraints on the identity of such cations. In certain embodiments, the cation associated with an anionic metal carbonyl compound comprises a simple metal cation such as those from Groups 1 or 2 of the periodic table (e.g. $Na^+$, $Li^+$, $K^+$, $Mg^{2+}$ and the like). In other embodiments a cation associated with a provided anionic metal carbonyl compound is a transition metal or transition metal complex. In other embodiments a cation associated with a provided anionic metal carbonyl compound is an organic cation. In certain embodiments a cation associated with a provided anionic metal carbonyl compound is a bulky non electrophilic cation such as an 'onium salt' (e.g. $Bu_4N^+$, $PPN^+$, $Ph_4P^+$ $Ph_4As^+$ and the like). In certain embodiments, a metal carbonyl anion is associated with a protonated nitrogen compound. In some embodiments, the cation associated with an anionic metal carbonyl compound comprises or is associated with a solid present in the carbonylation reaction zone. These solids may include inorganic materials or polymeric materials such as those which are described more fully below.

In certain embodiments, a provided metal carbonyl compound comprises a neutral metal carbonyl. In certain embodiments, such neutral metal carbonyl compounds have the general formula $QM_y(CO)_{w'}$, where Q, M, and y are as defined above and in the classes and subclasses described herein, and w' is an integer such as to provide a stable neutral metal carbonyl. In certain embodiments, the neutral metal carbonyl has the general formula $QM(CO)_{w'}$. In certain embodiments, the neutral metal carbonyl has the general formula $M(CO)^{w'}$. In certain embodiments, the neutral metal carbonyl has the general formula $QM_2(CO)_{w'}$. In certain embodiments, the neutral metal carbonyl has the general formula $M_2(CO)_{w'}$. In certain embodiments, the neutral metal carbonyl has the general formula $M_3(CO)_{w'}$. In certain embodiments, the neutral metal carbonyl has the general formula $M_4(CO)_{w'}$.

In certain embodiments, the neutral metal carbonyl is selected from the group consisting of: $Ti(CO)_7$; $V_2(CO)_{12}$; $Cr(CO)_6$; $Mo(CO)_6$; $W(CO)_6$ $Mn_2(CO)_{10}$, $Tc_2(CO)_{10}$, and $Re_2(CO)_{10}$ $Fe(CO)_5$, $Ru(CO)_5$ and $Os(CO)_5$ $Ru_3(CO)_{12}$, and $Os_3(CO)_{12}$ $Fe_3(CO)_{12}$ and $Fe_2(CO)_9$ $Co_4(CO)_{12}$, $Rh_4(CO)_{12}$, $Rh_6(CO)_{16}$, $Ir_4(CO)_{12}$, $Co_2(CO)_8$, and $Ni(CO)_4$.

In certain embodiments, one or more of the carbon monoxide ligands of any of the metal carbonyl compounds described above is replaced with a ligand Q. In certain embodiments, the ligand Q is present and represents a phosphine ligand. In certain embodiments, Q is present and represents a cyclopentadienyl (cp) ligand.

In certain embodiments, reaction systems and methods of the present invention comprise metal carbonyl hydrides (alternately referred to as hydrido metal carbonyl compounds). In certain embodiments, such compounds are provided as the metal carbonyl hydride. In other embodiments, the metal carbonyl hydride is generated in situ by reaction with hydrogen gas, or with a protic acid using methods known in the art (see for example *Chem. Rev.*, 1972, 72 (3), pp 231-281 DOI: 10.1021/cr60277a003, the entirety of which is incorporated herein by reference).

In certain embodiments, the metal carbonyl hydride (either as provided or generated in situ) comprises one or more of $HCo(CO)_4$, $HCoQ(CO)_3$, $HMn(CO)_5$, $HMn(CO)_4Q$, $HW(CO)_3Q$, $HRe(CO)_5$, $HMo(CO)_3Q$, $HOs(CO)_2Q$, $HMo(CO)_2Q_2$, $HFe(CO_2)Q$, $HW(CO)_2Q_2$, $HRuCOQ_2$, $H_2Fe(CO)_4$ or $H_2Ru(CO)_4$, where each Q is independently as defined above and in the classes and subclasses herein. In certain embodiments, the metal carbonyl hydride (either as provided or generated in situ) comprises $HCo(CO)_4$. In certain embodiments, the metal carbonyl hydride (either as provided or generated in situ) comprises $HCo(CO)_3PR_3$, where each R is independently an optionally substituted aryl group, an optionally substituted $C_{1-20}$ aliphatic group, a $C_{1-10}$ 10 alkoxy group, and an optionally substituted phenoxy group. In certain embodiments, the metal carbonyl hydride (either as provided or generated in situ) comprises $HCo(CO)_3cp$, where cp represents an optionally substituted cyclopentadienyl ligand. In certain embodiments, the metal carbonyl hydride (either as provided or generated in situ) comprises $HMn(CO)_5$. In certain embodiments, the metal carbonyl hydride (either as provided or generated in situ) comprises $H_2Fe(CO)_4$.

In certain embodiments, for any of the metal carbonyl compounds described above, M' comprises a transition metal. In certain embodiments, for any of the metal carbonyl compounds described above, M is selected from Groups 5 (Ti) to 10 (Ni) of the periodic table. In certain embodiments, M is a Group 9 metal. In certain embodiments, M is Co. In certain embodiments, M is Rh. In certain embodiments, M is Ir. In certain embodiments, M is Fe. In certain embodiments, M is Mn.

In certain embodiments, one or more ligands Q is present in a provided metal carbonyl compound. In certain embodiments, Q is a phosphine ligand. In certain embodiments, Q is a triaryl phosphine. In certain embodiments, Q is trialkyl phosphine. In certain embodiments, Q is a phosphite ligand. In certain embodiments, Q is an optionally substituted cyclopentadienyl ligand. In certain embodiments, Q is cp. In certain embodiments, Q is cp*.

In certain embodiments, the reaction zone into which the epoxide/carbon monoxide stream is fed comprises a solid metal carbonyl compound. In certain embodiments, the reaction zone comprises a solid-supported metal carbonyl compound. In certain embodiments, the solid supported metal carbonyl compound comprises a Group VIII metal carbonyl. In certain embodiments, the Group VIII metal carbonyl compound is selected from the group consisting of $Co_2(CO)_8$, $Co_4(CO)_{12}$, $Rh_4(CO)_{16}$, $Ir_4(CO)_{12}$ and mixtures of two or more of these. In certain embodiments, the solid supported metal carbonyl comprises a cobalt compound. In certain embodiments, the solid supported metal carbonyl comprises the moiety $Co(CO)_4^-$. In certain embodiments, the cobalt compound is $Co_2(CO)_8$ or a compound derived therefrom. In certain embodiments, the solid supported metal carbonyl is formed in situ from a suitable metal salt. In certain embodiments, the solid supported metal carbonyl is a compound resulting from the treatment of a metal or a metal salt adsorbed on a solid support and then treated with carbon monoxide under suitable conditions to convert at least a portion of the metal or salt to metal carbonyl compounds. In certain embodiments, the solid supported metal carbonyl is a compound resulting from the treatment of cobalt metal or a cobalt salt adsorbed on a solid support and then treated with carbon monoxide under suitable conditions to convert at least a portion of the cobalt or cobalt salt to cobalt carbonyl compounds.

The metal carbonyl concentration in the first reaction zone is not particularly limited, but in light of the balance between the conversion rate and selectivity, can range from about 0.005 to about 20 mmol of metal carbonyl per cubic centimeter of solid support volume. In certain embodiments, 0.1 to 5 mmol metal carbonyl is present per cc of solid support.

In certain embodiments, the first reaction zone also comprises other materials and/or additives such as metal salts, acids, bases, Lewis basic organic compounds Lewis acidic organic compounds Lewis acidic metal compounds and the like. In certain embodiments, such additives increase the rate of the epoxide carbonylation reaction relative to a reaction performed in a system lacking such additives. In certain embodiments, the additives comprise aluminum salts. In certain embodiments, the additives comprise zinc salts. In certain embodiments, the additives comprise transition metal salts. In certain embodiments, the additives comprise metal ligand complexes including organic ligands such as porphyrins, salens, and the like. In certain embodiments, the additives comprise high molecular weight alcohols, organic acids or amines. In certain embodiments, the additives comprise solid supported materials. In certain embodiments, the additives comprise solid-supported metal compounds, alcohols, organic acids or amines, or onium salts.

In certain embodiments, a solid support in the first reaction zone comprises an inorganic material. Many suitable inorganic supports are known in the art and a skilled artisan will recognize materials suitable for this purpose. In certain embodiments, suitable inorganic solid supports include, but are not limited to materials such as: silica, glass, alumina, zirconia, diatomaceous earth, metal oxides, metal salts, ceramics, clays, molecular sieves, kieselgur, titanium dioxide and the like. In certain embodiments, the solid support in the first reaction zone comprises silica gel. In certain embodiments, the solid support in the first reaction zone comprises alumina. In certain embodiments, the solid support in the first reaction zone comprises glass. In certain embodiments, the solid support in the first reaction zone comprises a ceramic. In certain embodiments, the solid support in the first reaction zone comprises diatomaceous earth.

In other embodiments, a solid support in the first reaction zone comprises a polymeric support. Suitable polymeric supports are known in the art and a skilled artisan will recognize materials suitable for this purpose. In certain embodiments, the polymeric supports may comprise polystyrene, divinylbenzene, polyvinylpyridine, polymethylmethacrylate, polyolefins, polytetrafluoroethylene, and combinations or derivatives thereof. In certain embodiments, the polymeric support comprises a cation exchange resin. In certain embodiments, the polymeric support comprises an anion exchange resin.

Carbonylation Reaction Conditions and Operation

In certain embodiments, the carbonylation reaction in the first reaction zone is operated at least partially in a gas phase. In these embodiments, the epoxide and carbon monoxide are fed into the reactor as gasses at an inlet and a product stream containing the beta lactone is removed from the reactor outlet. In certain embodiments, the beta lactone stream is also removed in the gas phase. In certain embodiments, the epoxide and carbon monoxide are fed into the reactor as gasses and the beta lactone stream is removed in the liquid phase. In these embodiments, the metal carbonyl compound may be present as a solid or solid-supported compound (heterogeneous catalysis).

The carbonylation reaction conditions are selected based on a number of factors to effect conversion of the epoxide to a beta-lactone. Temperature, pressure, and reaction time influence reaction speed and efficiency. Additionally the ratio of reactants to each other and to the catalyst effect reaction speed and efficiency.

In certain embodiments, the carbonylation in the first reaction zone is operated in a solution phase. In these embodiments, the epoxide and carbon monoxide are fed into the reactor at an inlet and a product stream containing the beta lactone is removed via gas sweeping or volatilization from the reactor outlet. Such a reactor can be operated as a boiling reactor designs and operating parameters for which are available in the art. In these embodiments, the metal carbonyl compound may be present as a soluble compound (homogenous catalysis), optionally dissolved in a solvent, or may be present as a solid or solid-supported compound (heterogeneous catalysis). The reactants may be fed as gas or a liquid or as combinations of these. In certain embodiments where the first reaction zone is operated in a solution phase, the reaction zone includes a high boiling reaction medium such as a high boiling organic solvent or an ionic liquid that remains in the reaction zone as the beta lactone is stripped from the reactor outlet.

The first reaction zone is operated under positive carbon monoxide pressure. In certain embodiments, a carbon monoxide partial pressure in the first reaction zone ranges from about 0.5 atmospheres to about 500 atmospheres. In certain embodiments, a carbon monoxide partial pressure in the first reaction zone ranges from about 0.5 atmospheres to about 350 atmospheres. In certain embodiments, the carbon monoxide partial pressure ranges from about 5 to about 100 atmospheres. In certain embodiments, the carbon monoxide partial pressure ranges from about 10 to about 50 atmospheres, from about 5 to about 20 atmospheres, from about 1 to about 10 atmospheres, or from about 5 to about 50 atmospheres. In some embodiments, the pressure can range from about 0.5 atmospheres to about 10 atmospheres (absolute). In some embodiments, the pressure can range from about 0.5 atmospheres to about 50 atmospheres (absolute). In some embodiments, the pressure can range from about 1 atmosphere to about 10 atmospheres (absolute). In some embodiments, the pressure can range from about 1 atmosphere to about 50 atmospheres (absolute). In some embodiments, the pressure can range from about 1 atmosphere to about 100 atmospheres (absolute). In some embodiments, the pressure can range from about 10 atmospheres to about 50 atmospheres (absolute). In some embodiments, the pressure can range from about 10 atmospheres to about 100 atmospheres (absolute). In some embodiments, the pressure can range from about 50 atmospheres to about 100 atmospheres (absolute). In some embodiments, the pressure can range from about 50 atmospheres to about 200 atmospheres (absolute). In some embodiments, the pressure can range from about 100 atmospheres to about 200 atmospheres (absolute). In some embodiments, the pressure can range from about 100 atmospheres to about 250 atmospheres (absolute). In some embodiments, the pressure can range from about 200 atmospheres to about 300 atmospheres (absolute). In some embodiments, the pressure can range from about 200 atmospheres to about 500 atmospheres (absolute). In some embodiments, the pressure can range from about 250 atmospheres to about 500 atmospheres (absolute).

In certain embodiments, the first reaction zone may comprise one or more carbon monoxide inlets (i.e. carbon monoxide sources independent from carbon monoxide that may be introduced admixed with epoxide in the epoxide feedstock stream). In certain embodiments, the epoxide and the carbon monoxide are introduced to the first reaction zone via separate inlets. In some embodiments, the reaction pressure is supplied entirely by the carbon monoxide. For example, the reactants and catalyst are charged to the reactor at atmospheric pressure, or under a vacuum, and carbon monoxide is added to the reactor to increase pressure to the reaction pressure. In some embodiments, all reactants are supplied to the reactor at reaction pressure.

In certain embodiments, the first reaction zone is at a temperature ranging from ambient to about 400° C. In certain embodiments, the first reaction zone is at a temperature ranging from about 50° C. to about 250° C. In certain embodiments, the temperature in the first reaction zone ranges from about 40° C. to about 200° C. In certain embodiments, the temperature in the first reaction zone ranges from about 50° C. to about 150° C. In certain embodiments, the temperature in the first reaction zone ranges from about 100° C. to about 220° C. In certain embodiments, the temperature in the first reaction zone ranges from about 60° C. to about 120° C. In certain embodiments, the temperature in the first reaction zone ranges from about 40° C. to about 80° C. In some embodiments, the temperature ranges from about 50° C. to 100° C. In some embodiments, the temperature ranges from about 50° C. to 200° C. In some embodiments, the temperature ranges from about 100° C. to 150° C. In some embodiments, the temperature ranges from about 100° C. to 200° C. In some embodiments, the temperature ranges from about 100° C. to 250° C. In some embodiments, the temperature ranges from about 150° C. to 250° C. In some embodiments, the temperature ranges from about 150° C. to 300° C. In some embodiments, the temperature ranges from about 200° C. to 300° C. In some embodiments, the reactants and catalyst are supplied to the reactor at standard temperature, and then heated in the reactor. In some embodiments, the reactants are pre-heated before entering the reactor.

In certain embodiments, the carbonylation in the first reaction zone is operated in a gas phase. In these embodiments, the epoxide and carbon monoxide are fed in the gas phase and the beta lactone produced in the reaction is removed via gas sweeping. In certain embodiments, the catalyst is a solid or solid supported. Generally, gas phase reactions are devoid of any solvent for reactants or catalyst.

In certain embodiments, a gas phase in the first reaction zone may comprise primarily carbon monoxide and epoxide substrate, while in other embodiments, additional gases or diluents may also be present. In certain embodiments, such diluents may include nitrogen, hydrogen, hydrocarbon gases or the like. In certain embodiments, the atmosphere in the first reaction zone is essentially free of oxygen. In certain embodiments, the atmosphere in the first reaction zone is essentially free of water. In certain embodiments, the atmosphere in the first reaction zone is essentially free of water and oxygen.

In some embodiments, the carbonylation reaction is performed in a continuous operation. The reactants are continuously fed to the first reaction zone. In some embodiments, the reactor includes a gas-entrainment impeller. The reactants may be fed to the reactor at standard temperature and pressure and then heated or pressurized to reaction conditions once in the reactor. The reactor itself may be any reactor conducive to continuous operation, including by not limited to a continuously stirred tank reactor or a tubular reactor. In some embodiments, the reactor is an adiabatic reactor, and/or an isothermal reactor. In some embodiments, the reactor pressure is constant. In some embodiments, the reactor pressure varies as the reaction progresses. In some embodiments, the reactor temperature varies as the reaction progress. In some embodiments, the reaction is performed in a batch operation. One of ordinary skill in the art will recognize the temperatures, pressures, catalyst ratios, concentrations of reactants, catalyst and solvents, flow rates can all be optimized or varied to achieve a given reaction outcome.

In some embodiments, the reaction is maintained for a period of time sufficient to allow complete, near complete reaction of the epoxide to beta-lactone or as complete as possible based on the reaction kinetics and or reaction conditions. In some embodiments, the reaction time is established as a residence time within the reactor. The reaction can be halted by reducing the reactor temperature or pressure, withdrawing a particular reactant or introducing a quenching compound. The reaction may be halted at any point or any percentage conversion of epoxide to beta-lactone. E.g., the reaction may be halted when 50% of the epoxide is converted to beta-lactone.

In one embodiment of the method, the epoxide comprises ethylene oxide, which is combined with carbon monoxide and reacted over a cobalt-based catalyst or precatalyst, such as dicobalt octacarbonyl, cobalt nitrate, cobalt acetate, cobalt chloride, or similar compounds, on a support consisting of silica gel, alumina, a zeolite or polymeric material, at a temperature of 50-200° C. and a pressure of 10-200 atmospheres to produce beta propiolactone. The reaction, being run with an excess of carbon monoxide, can result in almost total depletion of ethylene oxide. The less volatile beta propiolactone can be separated from unreacted carbon monoxide vapor stream by condensation and then fed directly to the next step. In another alternative, if the carbonylation reaction is run to the complete depletion of ethylene oxide, the entire effluent mixture of carbon monoxide containing the product beta propiolactone can be fed directly to the next step in a gaseous phase.

In certain embodiments, it may be desirable to operate the first reaction zone of the process in a series of stages. In one such embodiment, the first reaction zone (e.g., carbonylation) is separated into a plurality of individual reaction zones wherein each reaction zone achieves partial conversion of the epoxide in the feedstream to beta lactone. The unreacted epoxide and carbon monoxide exiting one reaction zone is then fed to the inlet of the next reaction zone. In certain embodiments, beta lactone formed in one stage is partially or wholly removed from the reaction stream prior to feed of the next stage. In this way, a balance can be achieved between consumption of epoxide feedstock and formation of lactone-derived byproducts since under some conditions higher conversion leads to greater formation of undesired byproducts. In certain embodiments, the individual reaction zones within the reactor are separated by a lower temperature zone from which the lactone condenses and is separated from the reaction stream before it enters the next reaction zone. In certain embodiments, the individual reaction zones in such a reactor decrease in size such that each stage is sized to efficiently accommodate the fraction of unreacted epoxide exiting the prior stage from which it is fed. In certain embodiments, the carbonylation reaction zone comprises between 2 and 20 individual reaction stages. In embodiments, where lactone is separated between stages, the resulting plurality of lactone streams can each feed the lactone conversion stage of the process, or they can be combined into one stream.

Carbonylation Reaction Products

As described above, the primary reaction product of the carbonylation reaction is a beta-lactone. Additionally, the product stream may contain other reaction by-products, un-reacted reactants, as well as catalyst and solvent. In some embodiments, the un-reacted reactants include epoxide or carbon monoxide. As such, the reaction may not proceed to completion and may be considered a partial reaction.

In some embodiments, the amount of un-reacted epoxide is sufficient to prevent the formation of a succinic anhydride, a potential carbonylation reaction byproduct. Without being bound by a particular theory, it is speculated that the second reaction converting the beta-lactone to succinic anhydride does not proceed, unless all of the epoxide is consumed. Thus, a remaining percent of the epoxide feed to the reactor that exits un-reacted appears to prevent the formation of succinic anhydride. In some embodiments, the product stream contains less than about 5% epoxide, less than about 3% epoxide, less than about 1% epoxide or less than about 0.1%. Note, all percentages are applicable on either a mole basis, weight basis, or volume basis, per reaction conditions may dictate.

In some embodiments, by-product formation includes the formation of succinic anhydride. In some embodiments, by-product formation includes the formation of one or more of the following compounds: crotonaldehyde, acrylic acid, 1,4 dioxane, acrylic acid dimers and trimers, 2-hydroxyethyl acrylate, 2,5 hexadienal, 3-oxacaprolactone, diethylene glycol monoacrylate, 3-hydroxypropionic acid, diethylene glycol diacrylate, 5-valerolactone and/or 2,6-dimethyl-1,3-dioxan-4-ol.

Lactone Conversion

Generally

In the next stage of processes of the invention, the effluent from the carbonylation reaction zone is fed to a second reaction zone where the beta lactone is subjected to conditions that convert it to a compound selected from the group consisting of: an alpha beta unsaturated acid, an alpha beta unsaturated ester, an alpha beta unsaturated amide, and a polymer. The second reaction stage is alternately referred to herein as the beta lactone conversion stage.

The beta lactone stream resulting from the carbonylation step is carried onto a lactone conversion step in a second reaction zone. The lactone conversion step is discussed in more detail below. The beta-lactone stream may optionally be processed in a number ways prior to the lactone conversion step. This processing can include, but is not limited to: heating, cooling, or compressing the stream; condensing the stream to a liquid state and carrying forward the liquid; adding a polymerization inhibitor to the stream; condensing selected components to a liquid state and carrying forward the remaining gaseous components; condensing selected components to a liquid state and carrying forward the liquefied components; scrubbing the stream to remove impurities; adding reactants/catalysts for lactone conversion reactions; and any combination of two or more of these.

In certain embodiments, the beta lactone is first separated from more volatile components in the product stream exiting the first reaction zone by condensing it to a liquid. This is easily achieved by cooling the product stream and/or increasing the pressure. In other embodiments, the entire effluent of the carbonylation stage is carried to the second reaction stage without any separation stage. This embodiment is particularly applicable if all of the epoxide has been consumed in which case the product stream exiting the carbonylation stage comprises essentially beta lactone and carbon monoxide (optionally mixed with other gases or volatile compounds if they were present at the feed or generated in situ).

Turning next to the lactone conversion step, the beta-lactone stream discussed above is carried onward to a second reaction zone to convert the beta lactone contained therein to any of several end products described in more detail below. As discussed above, in some embodiments, the beta-lactone stream may undergo additional processing steps between the carbonylation step and may enter the lactone conversion stage of the process as a gas or as a liquid. The lactone conversion step itself may be performed in either the gas phase or the liquid phase and may be performed neat, or in the presence of a carrier gas, solvent or other diluent.

In certain embodiments, the lactone conversion step is performed in a continuous flow format. In certain embodiments, the lactone conversion step is performed in a continuous flow format in the gas phase. In certain embodiments, the lactone conversion step is performed in a continuous flow format in the liquid phase. In certain embodiments, the lactone conversion step is performed in a liquid phase in a batch or semi-batch format. The lactone conversion step may be performed under a variety of conditions. In certain embodiments, the reaction may be performed in the presence of one or more catalysts that facilitate one or more steps in the transformation of the beta lactone to the end product.

In certain embodiments, the beta-lactone conversion stage is fed with a feed stream containing less than 5 percent epoxide (relative to beta lactone). In certain embodiments, the beta-lactone conversion stage is fed with a feed stream containing less than 2 percent epoxide. In certain embodiments, the beta-lactone conversion stage is fed with a feed stream containing less than 1 percent epoxide, less than 0.5 percent epoxide, less than 0.25 percent epoxide, less than 0.1 percent epoxide, or less than 0.05 percent epoxide. In certain embodiments, the beta-lactone conversion stage is fed with a feed stream containing essentially no unreacted epoxide. Note, all percentages are applicable on either a mole basis, weight basis, or volume basis, per reaction conditions may dictate.

In certain embodiments, the beta lactone conversion step comprises a solid catalyst and the conversion is conducted at least partially in the gas stage. In certain embodiments, the solid catalyst in the beta lactone conversion stage comprises a solid acid catalyst. In certain embodiments, the beta lactone is introduced as a liquid and contacted with the solid catalyst and the carboxylic acid (e.g., acrylic acid) or acid derivative (e.g., acrylic acid derivative) is removed as a gaseous stream. In other embodiments, the beta lactone is introduced as a gas, contacted with the solid catalyst and acrylic acid or an acrylic acid derivative is removed as a gaseous stream. In a specific embodiment, a mixture of beta propiolactone and water are contacted with a solid acid catalyst and gaseous acrylic acid is withdrawn from the reaction zone. In certain embodiments, a mixture of beta propiolactone and a lower alcohol are contacted with a solid acid catalyst and gaseous acrylate ester is withdrawn from the reaction zone.

In certain embodiments, the processes above are characterized in that the feed rates, reaction rates, and reactor sizes are scaled such that each subsequent stage in the process can utilize essentially all of the effluent from the previous stage. In certain embodiments, the methods include one or more steps of modulating one or more system parameters selected from the group consisting of: the ethylene and oxygen feed rates and/or ratios, the ethylene oxidation zone reaction temperature, the carbon monoxide feed rate, the carbonylation stage temperature, the carbonylation stage reaction pressure, the feed rate of one or more reactants entering the lactone conversion stage, the temperature and/or pressure of the lactone conversion stage, and a combination of any two or more of these parameters. In certain embodiments, this modulation of system parameters is performed such that the conversion rate per unit time of each stage matches that of the previous stage so that the effluent of the previous stage may be used directly to feed the subsequent stage. In certain embodiments, the methods include one or more steps of analyzing the effluent from one or more stages to assess its content. In certain embodiments, such analyzing steps include performing spectroscopy (e.g. infrared spectroscopy, nuclear magnetic resonance spectroscopy, ultraviolet or visible light spectroscopy and the like), chromatography (e.g. gas or liquid chromatography). In certain embodiments, such analyses are performed in a flow-through or stop-flow mode that provides real-time data on the chemical composition of the effluent. In certain embodiments, such data are used to provide a prompt to adjust one or more of the system parameters described above.

Carboxylic Acid Production

In certain embodiments, the product of the beta lactone conversion stage is an alpha beta unsaturated carboxylic acid or ester. There are a number of options possible for the way in which beta lactones can undergo thermolysis or alcoholysis to a carboxylic acid (e.g., acrylic acid) or an ester (e.g., acrylate esters), respectively. In one embodiment, beta propiolactone is fed directly to a reactor containing heated phosphoric acid, optionally including copper metal, a copper salt or other catalyst, to produce acrylic acid vapors that are continuously removed to avoid the formation of unwanted byproducts. The formation of acrylic acid can be run at atmospheric, super-atmospheric or sub-atmospheric pressures, at temperatures as high as 300° C. The acrylic acid produced is then condensed and purified by any of the methods known to one skilled in the art. Additional compounds useful in converting beta lactones to carboxylic acids include, but are not limited to sulfuric acid, zinc chloride, sodium bisulfate, boric acid, boric anhydride, phosphorus pentoxide as well as metallic catalysis such as, aluminum oxide, iron oxides, titanium oxides, etc., Further, basic catalysis may be use including calcium hydroxide, magnesium oxide, borax, disodiumphosphate, etc.

In certain embodiments, water may be added to this process to act as a catalyst. Without being bound by theory or limiting the scope of the present invention, it is believed water can aid this conversion by opening the beta lactone to form a beta hydroxy acid intermediate which then dehydrates to provide the desired alpha beta unsaturated acid and regenerate the water. The water may be added to the beta lactone stream before entering the second reaction zone, or it may be present in (or added independently to) the second reaction zone. In certain embodiments, the conversion of beta propiolactone to acrylic acid is performed using methods such as those disclosed in U.S. Pat. Nos. 3,176,042, 2,485,510, 2,623,067, 2,361,036 each of which is incorporated herein by reference. In other embodiments, the acrylate production may be base catalyzed, see for example *Journal of Organic Chemistry,* 57(1), 389-91(1992) and references therein, the entirety of which is incorporated herein by reference.

Many catalysts known in the art can be used, or adapted for this step. In some embodiments, conditions include reaction with dehydrating agents such as sulfuric acid, phosphoric acid or esters thereof as described in U.S. Pat. Nos. 2,352,641; 2,376,704; 2,449,995; 2,510,423; 2,623,067; 3,176,042, and in British Patent No. GB 994,091, the entirety of each of which is incorporated herein by reference.

In other embodiments, the lactone can be reacted with a halogenic compound to yield a beta halo acid, beta halo ester, or beta halo acid halide, which may then undergo dehydrohalogenation and/or solvolysis to afford the corresponding acrylic acid or acrylic ester. In certain embodiments, conditions disclosed in U.S. Pat. No. 2,422,728 (incorporated herein by reference) are used in this process.

Similarly, several methods can be employed to convert a beta lactone to an alpha beta unsaturated ester. For example, most methods use an alcohol in the beta lactone conversion stage (or added to the beta lactone stream before it is fed to this stage) to facilitate ring opening of the beta lactone to a beta hydroxy ester, or beta alkoxy acid, both of which can convert to alpha beta unsaturated esters. In certain embodiments, the lactone conversion step is performed in the presence of an alcohol. In certain embodiments, the lactone conversion step is performed in the presence of a $C_{1-20}$ alcohol. In certain embodiments, the lactone conversion step is performed in the presence of a $C_{1-8}$ alcohol. In certain embodiments, the lactone conversion step is performed in the presence of an alcohol selected from the group consisting of: methanol, ethanol, propanol, butanol, hexanol, and 2-ethyl-hexanol. In some embodiments, the alcohol used is a heptyl alcohol, an octyl alcohol, a nonyl alcohol, an n-decyl alcohol, an n-undecyl alcohol, a cetyl alcohol, an n-coded alcohol, an n-tetradecyl alcohol and other primary alcohols. Further, other alcohols can be used in the beta propiolactone conversion step, for example, sec-butyl alcohol, tert-butyl alcohol, allyl alcohol, beta-ethoxy-ethyl alcohol, diethylene glycol monoethyl either, cyclohexanol, furfuryl alcohol benzyl alcohol, and ethylene glycol among others as described above.

The beta lactone conversion is generally performed in the presence of a catalyst. For example, in some embodiments, the beta lactone is reacted with an alcohol in the presence of a dehydrating catalyst. Exemplary dehydrating catalysts include, but are not limited to: metal oxides (e.g., aluminum oxides, titanium oxides), zeolites, silica, and alumino-silicates, among others. Typically, such a conversion is performed in the liquid phase, and the product esters are isolated by distillation.

In some embodiments, the beta lactone conversion can be performed with activated carbon as a catalyst to produce alpha beta unsaturated esters. In some embodiments, the beta lactone is reacted with an alcohol in the gas phase and over an activated carbon catalyst to produce esters. The activated carbon can be supplied in any form, for example, powdered, granulated, extruded, beads, impregnated with other elements (e.g., iodine, silver, metallic cations, etc.).

In some embodiments, the reaction may include a polymerization inhibitor to prevent the formation of polymers. Exemplary polymerization inhibitors include copper, copper salts, hydroquinone, manganese, manganese salts, chromium, and chromium salts.

As described above, the beta lactone conversion step can be operated within a variety of temperature and pressure ranges when alpha beta unsaturated carboxylic acid or ester are the desired products. In some embodiments, the temperature can range from about 0° C. to about 300° C. In some embodiments, the temperature ranges from about 0° C. to 50° C. In some embodiments, the temperature ranges from about 0° C. to 100° C. In some embodiments, the temperature ranges from about 0° C. to 150° C. In some embodiments, the temperature ranges from about 0° C. to 200° C. In some embodiments, the temperature ranges from about 50° C. to 100° C. In some embodiments, the temperature ranges from about 50° C. to 150° C. In some embodiments, the temperature ranges from about 50° C. to 200° C. In some embodiments, the temperature ranges from about 100° C. to 150° C. In some embodiments, the temperature ranges from about 100° C. to 200° C. In some embodiments, the temperature ranges from about 100° C. to 250° C. In some embodiments, the temperature ranges from about 150° C. to 250° C. In some embodiments, the temperature ranges from about 150° C. to 300° C. In some embodiments, the temperature ranges from about 200° C. to 300° C.

In some embodiments, the pressure can range from about 0.01 atmospheres to about 500 atmospheres (absolute). In some embodiments, the pressure can range from about 0.01 atmospheres to about 10 atmospheres (absolute). In some embodiments, the pressure can range from about 0.01 atmospheres to about 50 atmospheres (absolute). In some embodiments, the pressure can range from about 1 atmosphere to about 10 atmospheres (absolute). In some embodiments, the pressure can range from about 1 atmosphere to about 50 atmospheres (absolute). In some embodiments, the pressure can range from about 1 atmosphere to about 100 atmospheres (absolute). In some embodiments, the pressure can range from about 10 atmospheres to about 50 atmospheres (absolute). In some embodiments, the pressure can range from about 10 atmospheres to about 100 atmospheres (absolute). In some embodiments, the pressure can range from about 50 atmospheres to about 100 atmospheres (absolute). In some embodiments, the pressure can range from about 50 atmospheres to about 200 atmospheres (absolute). In some embodiments, the pressure can range from about 100 atmospheres to about 200 atmospheres (absolute). In some embodiments, the pressure can range from about 100 atmospheres to about 250 atmospheres (absolute). In some embodiments, the pressure can range from about 200 atmospheres to about 300 atmospheres (absolute). In some embodiments, the pressure can range from about 200 atmospheres to about 500 atmospheres (absolute). In some embodiments, the pressure can range from about 250 atmospheres to about 500 atmospheres (absolute).

Applicants note that U.S. Pat. Nos. 2,466,501, 2,376,704 each of which is incorporated herein by reference in its entirety, describe methods of producing alpha beta unsaturated esters from beta lactones.

Unsaturated Amides

Alternatively, ammonia or an organic amine may be present in this stage to facilitate ring opening of the beta lactone to a beta hydroxy amide, which can be converted to alpha beta unsaturated amides. In certain embodiments, the lactone conversion is performed in the presence of ammonia to produce acrylamide. In certain embodiments, the lactone conversion is performed in the presence of a $C_{1-20}$ amine to produce N-substituted acrylamide derivatives. Exemplary amines include but are not limited to methyl amine, ethyl amine, propyl amines, butyl amines, amyl amines, and dialkyl amines. In some embodiments, the amine and the beta lactone are both soluble in water.

As described above, the beta lactone conversion step can be operated within a variety of temperature and pressure ranges when alpha beta unsaturated amides are the desired products. Some of the reactions are exothermic and therefore lower temperatures may be useful, as well as sufficient heat transfer to control reaction temperature. As described above, the beta lactone conversion step can be operated within a variety of temperature and pressure ranges when alpha beta unsaturated amides are the desired products. In some embodiments, the temperature can range from about 0° C. to about 300° C. In some embodiments, the temperature ranges from about 0° C. to 50° C. In some embodiments, the temperature ranges from about 0° C. to 100° C. In some embodiments, the temperature ranges from about 0° C. to 150° C. In some embodiments, the temperature ranges from about 0° C. to 200° C. In some embodiments, the temperature ranges from about 50° C. to 100° C. In some embodiments, the temperature ranges from about 50° C. to 150° C. In some embodiments, the temperature ranges from about 50° C. to 200° C. In some embodiments, the temperature ranges from about 100° C. to 150° C. In some embodiments, the temperature ranges from about 100° C. to 200° C. In some embodiments, the temperature ranges from about 100° C. to 250° C. In some embodiments, the temperature ranges from about 150° C. to 250° C. In some embodiments, the temperature ranges from about 150° C. to 300° C. In some embodiments, the temperature ranges from about 200° C. to 300° C.

In some embodiments, the pressure can range from about 0.01 atmospheres to about 500 atmospheres (absolute). In some embodiments, the pressure can range from about 0.01 atmospheres to about 10 atmospheres (absolute). In some embodiments, the pressure can range from about 0.01 atmospheres to about 50 atmospheres (absolute). In some embodiments, the pressure can range from about 1 atmosphere to about 10 atmospheres (absolute). In some embodiments, the pressure can range from about 1 atmosphere to about 50 atmospheres (absolute). In some embodiments, the pressure can range from about 1 atmosphere to about 100 atmospheres (absolute). In some embodiments, the pressure can range from about 10 atmospheres to about 50 atmospheres (absolute). In some embodiments, the pressure can range from about 10 atmospheres to about 100 atmospheres (absolute). In some embodiments, the pressure can range from about 50 atmospheres to about 100 atmospheres (absolute). In some embodiments, the pressure can range from about 50 atmospheres to about 200 atmospheres (absolute). In some embodiments, the pressure can range from about 100 atmospheres to about 200 atmospheres (absolute). In some embodiments, the pressure can range from about 100 atmospheres to about 250 atmospheres (absolute). In some embodiments, the pressure can range from about 200 atmospheres to about 300 atmospheres (absolute). In some embodiments, the pressure can range from about 200 atmospheres to about 500 atmospheres (absolute). In some embodiments, the pressure can range from about 250 atmospheres to about 500 atmospheres (absolute).

Applicants note that U.S. Pat. No. 2,548,155, which is incorporated herein by reference in its entirety, describes methods of producing alpha beta unsaturated amides from beta lactones.

Polymerization

In another embodiment of the present invention, the beta lactone from the carbonylation step is fed into a subsequent stage comprising a polymerization catalyst. This provides the opportunity to produce biodegradable polyesters such as poly(3-hydroxy butyrate) (P-3HB), and poly(propiolactone) without the need to handle and transport beta lactones. Many catalysts are known for the ring-opening polymerization of lactones (such as caprolactone and beta lactones). Any such catalyst can be employed in the present process.

Catalysts suitable for the ring-opening polymerization step of the methods disclosed herein are disclosed, for example, in: Journal of the American Chemical Society (2002), 124(51), 15239-15248 *Macromolecules*, vol. 24, No. 20, pp. 5732-5733, *Journal of Polymer Science*, Part A-1, vol. 9, No. 10, pp. 2775-2787; Inoue, S., Y. Tomoi, T. Tsuruta & J. Furukawa; *Macromolecules*, vol. 26, No. 20, pp. 5533-5534; Macromolecules, vol. 23, No. 13, pp. 3206-3212; *Polymer Preprints* (1999), 40(1), 508-509; Macromolecules, vol. 21, No. 9, pp. 2657-2668; and *Journal of Organometallic Chemistry*, vol. 341, No. 1-3, pp. 83-9; and in U.S. Pat. Nos. 3,678,069, 3,169,945, 6,133,402; 5,648,452; 6,316,590; 6,538,101; and 6,608,170. The entirety of each of which is hereby incorporated herein by reference.

In certain embodiments where the beta lactone conversion step comprises polymerizing the beta lactone, the step includes the step of contacting the beta lactone with a polymerization catalyst, optionally in the presence of one or more solvents. Suitable solvents can include, but are not limited to: hydrocarbons, ethers, esters, ketones, nitriles, amides, sulfones, halogenated hydrocarbons, and the like. In certain embodiments, the solvent is selected such that the polymer formed is soluble in the reaction medium.

In certain embodiments where the beta lactone conversion step comprises polymerizing the beta lactone to form a polyester, the step comprises a continuous polymerization. Such continuous polymerizations can be conducted in a continuous stirred tank reactor or a plug flow reactor such that polymer or polymer solution is withdrawn at essentially the same rate it is formed. Polymerization of lactones to polyester can be performed with a number of polymerization initiators including but not limited to alcohols, amines, polyols, polyamines, and diols, amongst others. Further a variety of catalysts may be used in the polymerization reaction, including by not limited to metals (e.g., lithium, sodium, potassium, magnesium, calcium, zinc, aluminum, titanium, cobalt, etc.) metal oxides, carbonates of alkali- and alkaline earth metals, borates, silicates, of various metals.

As described above, the beta lactone conversion step can be operated within a variety of temperature and pressure ranges when polyesters are the desired products. As described above, the beta lactone conversion step can be operated within a variety of temperature and pressure ranges when alpha beta unsaturated carboxylic acid or ester are the desired products. In some embodiments, the temperature can range from about 0° C. to about 300° C. In some embodiments, the temperature ranges from about 0° C. to 50° C. In some embodiments, the temperature ranges from about 0° C.

to 100° C. In some embodiments, the temperature ranges from about 0° C. to 150° C. In some embodiments, the temperature ranges from about 0° C. to 200° C. In some embodiments, the temperature ranges from about 50° C. to 100° C. In some embodiments, the temperature ranges from about 50° C. to 150° C. In some embodiments, the temperature ranges from about 50° C. to 200° C. In some embodiments, the temperature ranges from about 100° C. to 150° C. In some embodiments, the temperature ranges from about 100° C. to 200° C. In some embodiments, the temperature ranges from about 100° C. to 250° C. In some embodiments, the temperature ranges from about 150° C. to 250° C. In some embodiments, the temperature ranges from about 150° C. to 300° C. In some embodiments, the temperature ranges from about 200° C. to 300° C.

In some embodiments, the pressure can range from about 0.01 atmospheres to about 500 atmospheres (absolute). In some embodiments, the pressure can range from about 0.01 atmospheres to about 10 atmospheres (absolute). In some embodiments, the pressure can range from about 0.01 atmospheres to about 50 atmospheres (absolute). In some embodiments, the pressure can range from about 1 atmosphere to about 10 atmospheres (absolute). In some embodiments, the pressure can range from about 1 atmosphere to about 50 atmospheres (absolute). In some embodiments, the pressure can range from about 1 atmosphere to about 100 atmospheres (absolute). In some embodiments, the pressure can range from about 10 atmospheres to about 50 atmospheres (absolute). In some embodiments, the pressure can range from about 10 atmospheres to about 100 atmospheres (absolute). In some embodiments, the pressure can range from about 50 atmospheres to about 100 atmospheres (absolute). In some embodiments, the pressure can range from about 50 atmospheres to about 200 atmospheres (absolute). In some embodiments, the pressure can range from about 100 atmospheres to about 200 atmospheres (absolute). In some embodiments, the pressure can range from about 100 atmospheres to about 250 atmospheres (absolute). In some embodiments, the pressure can range from about 200 atmospheres to about 300 atmospheres (absolute). In some embodiments, the pressure can range from about 200 atmospheres to about 500 atmospheres (absolute). In some embodiments, the pressure can range from about 250 atmospheres to about 500 atmospheres (absolute).

Applicants note that U.S. Pat. Nos. 3,169,945 & 3,678,069, each of which is incorporated herein by reference in its entirety, describe methods of producing polyesters from beta lactones.

Specific Integrated Embodiments

Combining concepts and details described above, the present invention encompasses the following methods:

A method for the synthesis of acrylic acid comprising the steps of:
1) providing a gaseous feedstock stream comprising ethylene oxide and carbon monoxide;
2) directing the feedstock stream to a first reaction zone where it is contacted with a metal carbonyl compound and where at least a portion of the ethylene oxide is converted to a product stream comprising beta propiolactone;
3) optionally adding water to the product stream comprising beta propiolactone;
4) directing the product stream comprising beta propiolactone to a second reaction zone where it is contacted with a catalyst which catalyzes the conversion of beta propiolactone to acrylic acid;
5) withdrawing an acrylic acid product stream from the second reaction zone; and
6) isolating acrylic acid from the product stream.

A method for the synthesis of acrylate esters comprising the steps of:
1) providing a gaseous feedstock stream comprising ethylene oxide and carbon monoxide;
2) directing the feedstock stream to a first reaction zone where it is contacted with a metal carbonyl compound and at least a portion of the ethylene oxide is converted to a product stream comprising beta propiolactone;
3) adding a $C_{1-8}$ alcohol to the product stream comprising beta propiolactone;
4) directing the product stream comprising beta propiolactone and the $C_{1-8}$ alcohol to a second reaction zone where it is contacted with a catalyst which catalyzes the conversion of beta propiolactone and the $C_{1-8}$ alcohol to the corresponding acrylic acid ester;
5) withdrawing an acrylic acid ester product stream from the second reaction zone; and
6) isolating acrylic acid ester from the product stream.

A method for the synthesis of polypropiolactone comprising the steps of:
1) providing a gaseous feedstock stream comprising ethylene oxide and carbon monoxide;
2) directing the feedstock stream to a first reaction zone where it is contacted with a metal carbonyl compound and at least a portion of the ethylene oxide is converted to a product stream comprising beta propiolactone;
3) directing the product stream comprising beta propiolactone to a polymerization reactor containing a suitable solvent and a polymerization catalyst;
4) withdrawing a polypropiolactone product stream from the polymerization reactor; and
5) isolating polypropiolactone from the product stream.

In certain embodiments, the above methods for the synthesis of acrylic acid, acrylate esters, or polypropiolactone comprise the additional step before step (1) of oxidizing ethylene to provide ethylene oxide. In certain embodiments, such a step comprises the substeps of contacting ethylene with oxygen in an ethylene oxidation reactor in the presence of a suitable catalyst to convert at least a portion of the ethylene to ethylene oxide, withdrawing a gaseous ethylene oxide stream from the ethylene oxidation reactor; and combining the gaseous ethylene oxide stream with carbon monoxide to provide the feedstock stream.

In certain embodiments, in the above methods for the synthesis of acrylic acid, acrylate esters, or polypropiolactone, the step of directing the product stream comprising beta propiolactone to the next reaction step comprises feeding the beta propiolactone as a gas. In certain embodiments, the step of directing the product stream comprising beta propiolactone to the next reaction step comprises feeding the beta propiolactone as a liquid.

A method for the synthesis of poly-3-hydroxybutyrate comprising the steps of:
1) providing a gaseous feedstock stream comprising propylene oxide and carbon monoxide;
2) directing the feedstock stream to a first reaction zone where it is contacted with a metal carbonyl compound and at least a portion of the propylene oxide is converted to a product stream comprising beta butyrolactone;

3) directing the product stream comprising beta butyrolactone to a polymerization reactor containing a suitable solvent and a polymerization catalyst;
4) withdrawing a poly-3-hydroxybutyrate product stream from the polymerization reactor; and
5) isolating poly-3-hydroxybutyrate from the product stream.

In certain embodiments, the feedstock stream provided in the above method for the synthesis of poly-3-hydroxybutyrate comprises enantio-enriched propylene oxide.

In certain embodiments, in the above methods for the synthesis of acrylic acid, acrylate esters, polypropiolactone, or poly-3-hydroxybutyrate, the metal carbonyl compound in the first reaction zone comprises a cobalt carbonyl compound. In certain embodiments, the metal carbonyl compound in the first reaction zone comprises a rhodium carbonyl compound.

II) Systems of the Invention

In another aspect, the present invention provides systems for the synthesis of acrylic acid or acrylic acid derivatives. In certain embodiments, the system comprises:
  a first reactor, comprising an inlet fed by an epoxide source and a carbon monoxide source; a catalyst bed comprising one or more metal carbonyl compounds; and a reactor outlet which provides an outlet stream comprising a beta lactone; and
  a second reactor comprising an inlet fed by the outlet stream of the first reaction zone; a catalyst bed comprising an acid catalyst where the water and the beta lactone are reacted to provide an alpha beta unsaturated acid; and a reactor outlet which provides a product stream comprising alpha beta unsaturated acid.

In certain embodiments, the second reactor in the system above further comprises a water inlet. In certain embodiments, the system above further comprises a condenser with an inlet fed by the product stream of the second reactor and an outlet from which a liquid alpha beta unsaturated acid product is withdrawn.

In another embodiment, the present invention provides systems for the synthesis of acrylic acid esters. In certain embodiments, the system comprises:
  a first reactor, comprising an inlet fed by an epoxide source and a carbon monoxide source; a catalyst bed comprising one or more metal carbonyl compounds; and a reactor outlet which provides an outlet stream comprising a beta lactone; and
  a second reactor comprising a first inlet fed by the outlet stream of the first reaction zone; a second inlet fed with a $C_{1-8}$ alcohol, a catalyst bed comprising a catalyst where the alcohol and the beta lactone are reacted to provide an alpha beta unsaturated ester; and a reactor outlet which provides a product stream comprising alpha beta unsaturated ester.

In another embodiment, the present invention provides systems for the synthesis of polyesters. In certain embodiments, the system comprises:
  a first reactor, comprising an inlet fed by an epoxide source and a carbon monoxide source; a catalyst bed comprising one or more metal carbonyl compounds; and a reactor outlet which provides an outlet stream comprising a beta lactone; and
  a second reactor comprising a first inlet fed by the outlet stream of the first reaction zone; a catalyst solution comprising a polymerization catalyst and a solvent, and a reactor outlet, which provides a product stream comprising a solution of polyester polymer.

Some of the optional but non-limiting configurations of the processes described above are shown in FIGS. 1 and 2.

In FIG. 1, carbon monoxide (1) and an epoxide (e.g., ethylene oxide (2)) are mixed and fed the carbonylation reactor (3) which contains a supported catalyst (e.g., cobalt catalyst). The configuration of the reactor can take many forms, as one skilled in the art recognizes, including a catalyst bed or catalyst filled tubes, which are situated within containing vessels, etc. Provision for heat transfer, temperature and pressure control, etc., are details that are not included but as one skilled in the art would recognized, are a vital part of any reactor system design.

The product gas (4) contains unreacted carbon monoxide and product beta lactone (e.g., beta propiolactone). In a particular mode of operation, the reaction is run with a large excess of carbon monoxide, the effluent gas (4) contains no (or only minor amounts of) residual unreacted epoxide.

The effluent gas (4) is then fed directly to the thermolysis reactor (5) which contains a suitable catalyst for the conversion of the beta lactone (e.g., beta propiolactone) to a carboxylic acid (e.g., acrylic acid). For example, the thermolysis reactor could be a vessel containing a hot phosphoric acid/catalyst solution at a suitable temperature and pressure that acrylic acid is produced. As the acid is formed, it is removed as a vapor product, which is subsequently separated by known methods into gaseous stream containing mainly unreacted carbon monoxide (9), and a crude carboxylic acid product (10) which would undergo further purification to the required specifications by methods well known to those in the field. Alternately, thermolysis reactor could comprise a heterogeneous catalyst such as a solid supported acid and the conversion of beta lactone (e.g., beta propiolactone) to a carboxylic acid (e.g., acrylic acid) can be performed with the lactone and the carboxylic acid substantially in the gas phase.

A purge stream (8) taken from the thermolysis reactor provides a way of preventing the buildup of heavy byproducts and spent catalyst. Make-up catalyst (not shown in FIG. 1) would periodically be added to replenish the reaction medium.

Figure 2:
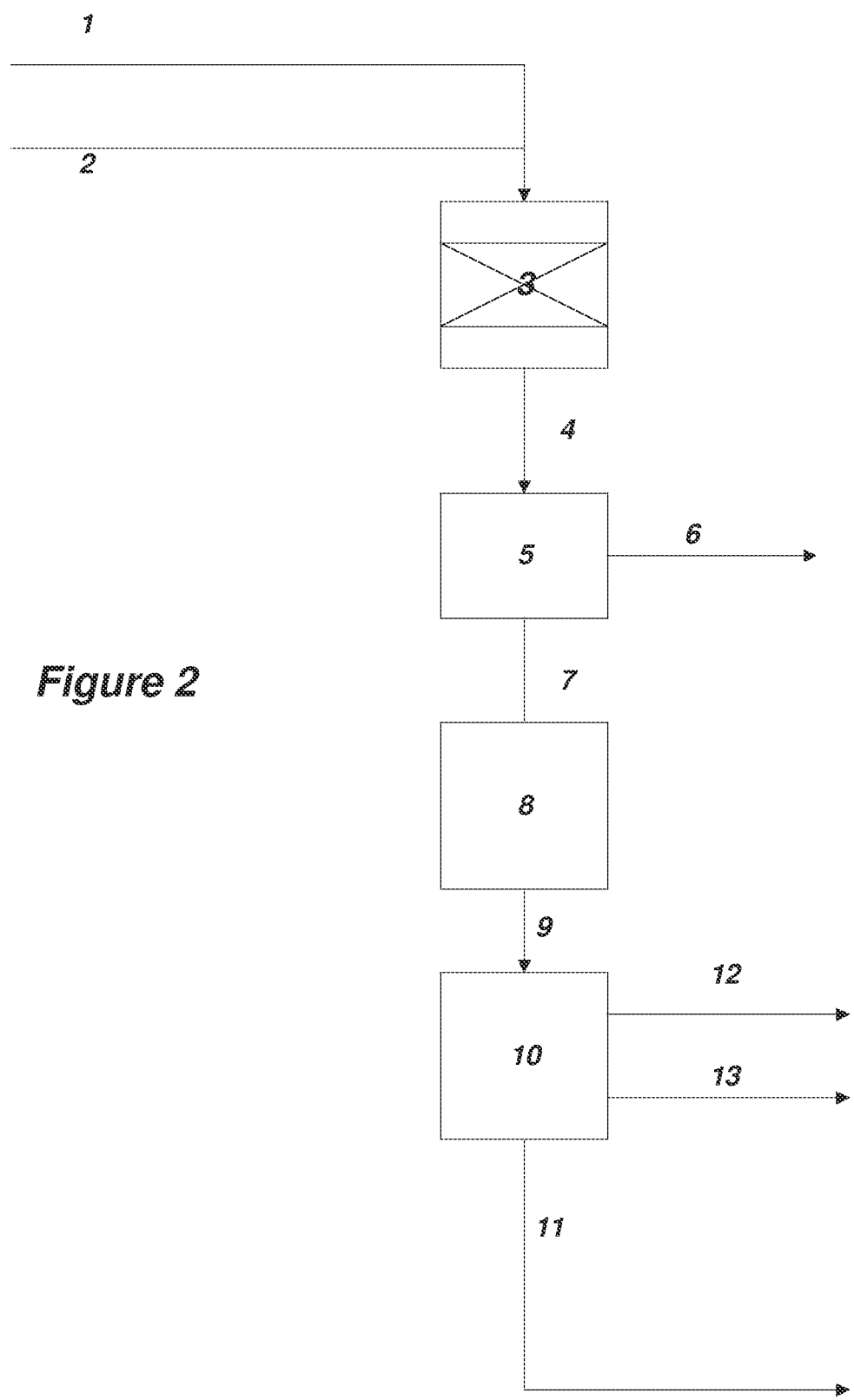
FIG. 2 shows a process schematic for production of beta lactone from an epoxide using a supported catalyst with a provision for capturing unreacted feedstocks downstream of the carbonylation reactor.

FIG. 2 shows another configuration, similar to FIG. 1, but includes provision for separating unreacted carbon monoxide and epoxide (e.g., ethylene oxide) (6) between the carbonylation reactor (3) and the thermolysis reactor (8) by means of a condensation step (5) using processing equipment well known to those skilled in the art. For this case, the reaction of carbon monoxide (1) and ethylene oxide (2) in the carbonylation reactor (3) does not necessarily go to the complete reaction of ethylene oxide. Condensed beta lactone (e.g., beta propiolactone) (7) is fed directly to the thermolysis reactor (8) for the conversion to acrylic acid in a manner analogous to that explained in the configuration of FIG. 1. As would be typical of such processes, there would still be provision for the purging of light gaseous products (12), the separation of a crude acrylic acid (13) for further purification to the required specification and the purging of heavy byproducts and spent catalyst (11).

FIGS. 1 and 2 are just illustrative but not limiting to the depiction of possible configurations of the invention.

The benefits of this invention include the ability to produce valued industrial products, such as acrylic acid and acrylic esters, from carbon monoxide, a reactant that can be derived from any number of feedstocks, including natural gas, oil, coal, biomass or waste products, in an efficient manner without the potential for personal or environmental harm associated with previous efforts to utilize this overall route.

OTHER EMBODIMENTS

The foregoing has been a description of certain nonlimiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

The invention claimed is:

1. A method for producing acrylic acid, comprising:
    contacting ethylene oxide with carbon monoxide in the presence of a metal carbonyl compound supported on a solid support in a first reaction zone;
    carbonylating at least a portion of the ethylene oxide in the first reaction zone to produce beta-propiolactone;
    directing the beta-propiolactone to a second reaction zone; and
    converting at least a portion of the beta-propiolactone in the second reaction zone to acrylic acid in the presence of a catalyst, wherein the conversion of the beta-propiolactone to the acrylic acid is performed in a continuous flow format.

2. The method of claim 1, further comprising isolating the acrylic acid from the second reaction zone.

3. The method of claim 1, where the catalyst in the second reaction zone comprises phosphoric acid, phosphorous pentoxide, aluminum oxide, iron oxide, titanium oxide, calcium hydroxide, magnesium hydroxide, or disodium phosphate, or any combinations thereof.

4. The method of claim 1, wherein the solid support comprises a polymeric support.

5. The method of claim 4, wherein the polymeric support comprises polystyrene, divinylbenzene, polyvinylpyridine, polymethylmethacrylate, a polyolefin, or polytetrafluoroethylene, or any combinations thereof.

6. The method of claim 1, wherein the solid support comprises an inorganic solid.

7. The method of claim 1, wherein the solid support comprises silica, glass, zirconia, diatomaceous earth, a metal oxide, a metal salt, a ceramic, a clay, a molecular sieve, kieselgur, or titanium dioxide, or any combinations thereof.

8. The method of claim 1, wherein the metal carbonyl compound has a formula $[QM_y(CO)_w]^x$, wherein:
    Q is any ligand or more than one ligand and need not be present;
    M is a metal atom;
    y is an integer from 1 to 6 inclusive;
    w is a number such as to provide the stable metal carbonyl; and
    x is an integer from −3 to +3 inclusive.

9. The method of claim 8, wherein M is Ti, Cr, Mn, Fe, Ru, Co, Rh, Ni, Pd, Cu, Zn, Al, Ga or In.

10. The method of claim 8, wherein M is Co.

11. The method of claim 1, wherein the metal carbonyl compound comprises $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, or $Ni(CO)_4$.

12. The method of claim 1, wherein the metal carbonyl compound comprises $Co_2(CO)_8$.

13. The method of claim 1, wherein the metal carbonyl compound comprises $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, or $[Mn(CO)_5]^-$.

14. The method of claim 1, wherein the metal carbonyl compound comprises $[Co(CO)_4]^-$.

15. A method for producing an acrylate ester, comprising:
    contacting ethylene oxide with carbon monoxide in the presence of a metal carbonyl compound supported on a solid support in a first reaction zone;
    carbonylating at least a portion of the ethylene oxide in the first reaction zone to produce beta-propiolactone;
    directing the beta-propiolactone and a $C_{1-20}$ alcohol to a second reaction zone; and
    converting at least a portion of the beta-propiolactone and the $C_{1-20}$ alcohol in the second reaction zone to an acrylate ester in the presence of a catalyst, wherein the conversion of the beta-propiolactone and $C_{1-20}$ alcohol to the acrylate ester is performed in a continuous flow format.

16. The method of claim 15, further comprising isolating the acrylate ester from the second reaction zone.

17. The method of claim 15, wherein the $C_{1-20}$ alcohol is methanol, ethanol, propanol, butanol, hexanol, 2-ethylhexanol, allyl alcohol, beta-ethoxy-ethyl alcohol, heptyl alcohol, octyl alcohol, nonyl alcohol, n-decyl alcohol, n-undecyl alcohol, cetyl alcohol, n-dodecyl alcohol, n-tetradecyl alcohol, diethylene glycol monoethyl ether, cyclohexanol, furfuryl alcohol, benzyl alcohol, or ethylene glycol, or any combinations thereof.

18. The method of claim 15, wherein the $C_{1-20}$ alcohol is a $C_{1-8}$ alcohol.

19. The method of claim 15, wherein the catalyst in the second reaction zone comprises a metal oxide, zeolite, silica, alumino-silicate, or activated carbon, or any combinations thereof.

20. The method of claim 15, wherein the solid support comprises a polymeric support.

21. The method of claim 20, wherein the polymeric support comprises polystyrene, divinylbenzene, polyvinylpyridine, polymethylmethacrylate, a polyolefin, or polytetrafluoroethylene, or any combinations thereof.

22. The method of claim 15, wherein the solid support comprises an inorganic solid.

23. The method of claim 15, wherein the solid support comprises silica, glass, zirconia, diatomaceous earth, a metal oxide, a metal salt, a ceramic, a clay, a molecular sieve, kieselgur, or titanium dioxide, or any combinations thereof.

24. The method of claim 15, wherein the metal carbonyl compound has a formula $[QM_y(CO)_w]^x$, wherein:
    Q is any ligand or more than one ligand and need not be present;
    M is a metal atom;
    y is an integer from 1 to 6 inclusive;
    w is a number such as to provide the stable metal carbonyl; and
    x is an integer from −3 to +3 inclusive.

25. The method of claim 24, wherein M is Ti, Cr, Mn, Fe, Ru, Co, Rh, Ni, Pd, Cu, Zn, Al, Ga or In.

26. The method of claim 24, wherein M is Co.

27. The method of claim 15, wherein the metal carbonyl compound comprises $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, or $Ni(CO)_4$.

28. The method of claim 15, wherein the metal carbonyl compound comprises $Co_2(CO)_8$.

29. The method of claim 15, wherein the metal carbonyl compound comprises $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, or $[Mn(CO)_5]^-$.

30. The method of claim 15, wherein the metal carbonyl compound comprises $[Co(CO)_4]^-$.

31. A method for producing polypropiolactone, comprising:
contacting ethylene oxide with carbon monoxide in the presence of a metal carbonyl compound supported on a solid support in a first reaction zone;
carbonylating at least a portion of the ethylene oxide in the first reaction zone to produce beta-propiolactone;
directing the beta-propiolactone to a second reaction zone; and
converting at least a portion of the beta-propiolactone in the second reaction zone to polypropiolactone in the presence of a catalyst, wherein the conversion of the beta-propiolactone to the polypropiolactone is performed in a continuous flow format.

32. The method of claim 31, further comprising isolating the polypropiolactone from the second reaction zone.

33. The method of claim 31, wherein the solid support comprises a polymeric support.

34. The method of claim 33, wherein the polymeric support comprises polystyrene, divinylbenzene, polyvinylpyridine, polymethylmethacrylate, a polyolefin, or polytetrafluoroethylene, or any combinations thereof.

35. The method of claim 31, wherein the solid support comprises an inorganic solid.

36. The method of claim 31, wherein the solid support comprises silica, glass, zirconia, diatomaceous earth, a metal oxide, a metal salt, a ceramic, a clay, a molecular sieve, kieselgur, or titanium dioxide, or any combinations thereof.

37. The method of claim 31, wherein the metal carbonyl compound has a formula $[QM_y(CO)_w]^x$, wherein:
Q is any ligand or more than one ligand and need not be present;
M is a metal atom;
y is an integer from 1 to 6 inclusive;
w is a number such as to provide the stable metal carbonyl; and
x is an integer from −3 to +3 inclusive.

38. The method of claim 37, wherein M is Ti, Cr, Mn, Fe, Ru, Co, Rh, Ni, Pd, Cu, Zn, Al, Ga or In.

39. The method of claim 37, wherein M is Co.

40. The method of claim 31, wherein the metal carbonyl compound comprises $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, or $Ni(CO)_4$.

41. The method of claim 31, wherein the metal carbonyl compound comprises $Co_2(CO)_8$.

42. The method of claim 31, wherein the metal carbonyl compound comprises $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, or $[Mn(CO)_5]^-$.

43. The method of claim 31, wherein the metal carbonyl compound comprises $[Co(CO)_4]^-$.

44. A method for producing an acrylamide, comprising:
contacting ethylene oxide with carbon monoxide in the presence of a metal carbonyl compound supported on a solid support in a first reaction zone;
carbonylating at least a portion of the ethylene oxide in the first reaction zone to produce beta-propiolactone;
directing the beta-propiolactone and an organic amine to a second reaction zone; and
converting at least a portion of the beta-propiolactone and the organic amine in the second reaction zone to an acrylamide, wherein the conversion of the beta-propiolactone and the organic amine to the acrylamide is performed in a continuous flow format.

45. The method of claim 44, further comprising isolating the acrylamide from the second reaction zone.

46. The method of claim 44, wherein the organic amine is ammonia.

47. The method of claim 44, wherein the solid support comprises a polymeric support.

48. The method of claim 47, wherein the polymeric support comprises polystyrene, divinylbenzene, polyvinylpyridine, polymethylmethacrylate, a polyolefin, or polytetrafluoroethylene, or any combinations thereof.

49. The method of claim 44, wherein the solid support comprises an inorganic solid.

50. The method of claim 44, wherein the solid support comprises silica, glass, zirconia, diatomaceous earth, a metal oxide, a metal salt, a ceramic, a clay, a molecular sieve, kieselgur, or titanium dioxide, or any combinations thereof.

51. The method of claim 44, wherein the metal carbonyl compound has a formula $[QM_y(CO)_w]^x$, wherein:
Q is any ligand or more than one ligand and need not be present;
M is a metal atom;
y is an integer from 1 to 6 inclusive;
w is a number such as to provide the stable metal carbonyl; and
x is an integer from −3 to +3 inclusive.

52. The method of claim 51, wherein M is Ti, Cr, Mn, Fe, Ru, Co, Rh, Ni, Pd, Cu, Zn, Al, Ga or In.

53. The method of claim 51, wherein M is Co.

54. The method of claim 44, wherein the metal carbonyl compound comprises $Ti(CO)_7$, $V_2(CO)_{12}$, $Cr(CO)_6$, $Mo(CO)_6$, $W(CO)_6$, $Mn_2(CO)_{10}$, $Tc_2(CO)_{10}$, $Re_2(CO)_{10}$, $Fe(CO)_5$, $Ru(CO)_5$, $Os(CO)_5$, $Ru_3(CO)_{12}$, $Os_3(CO)_{12}$, $Fe_3(CO)_{12}$, $Fe_2(CO)_9$, $Co_4(CO)_{12}$, $Rh_4(CO)_{12}$, $Rh_6(CO)_{16}$, $Ir_4(CO)_{12}$, $Co_2(CO)_8$, or $Ni(CO)_4$.

55. The method of claim 44, wherein the metal carbonyl compound comprises $Co_2(CO)_8$.

56. The method of claim 44, wherein the metal carbonyl compound comprises $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, or $[Mn(CO)_5]^-$.

57. The method of claim 44, wherein the metal carbonyl compound comprises $[Co(CO)_4]^-$.

\* \* \* \* \*